US007129048B2

(12) United States Patent
Bruchez et al.

(10) Patent No.: US 7,129,048 B2
(45) Date of Patent: *Oct. 31, 2006

(54) LOOP PROBE HYBRIDIZATION ASSAY FOR POLYNUCLEOTIDE ANALYSIS

(75) Inventors: Marcel P. Bruchez, Fremont, CA (US); Jennifer Lai, Mountain View, CA (US); Vince Phillips, Sunnyvale, CA (US); Andrew R. Watson, Belmont, CA (US); Edith Wong, Danville, CA (US)

(73) Assignee: Invitrogen Corporation, Carlsbad, CA (US)

( * ) Notice: Subject to any disclaimer, the term of this patent is extended or adjusted under 35 U.S.C. 154(b) by 456 days.

This patent is subject to a terminal disclaimer.

(21) Appl. No.: 10/716,063

(22) Filed: Nov. 17, 2003

(65) Prior Publication Data
US 2004/0171039 A1 Sep. 2, 2004

Related U.S. Application Data

(63) Continuation of application No. 09/815,510, filed on Mar. 22, 2001, now Pat. No. 6,653,080.

(60) Provisional application No. 60/237,000, filed on Sep. 29, 2000, provisional application No. 60/191,227, filed on Mar. 22, 2000.

(51) Int. Cl.
C12Q 1/68 (2006.01)
C12P 19/34 (2006.01)
C07H 21/04 (2006.01)

(52) U.S. Cl. .................... 435/6; 435/91.2; 536/24.3

(58) Field of Classification Search .................... 435/6, 435/91.2; 536/24.3
See application file for complete search history.

(56) References Cited

U.S. PATENT DOCUMENTS

| 5,545,531 A | 8/1996 | Rava et al. |
| 5,691,153 A | 11/1997 | Recker et al. |
| 5,858,676 A | 1/1999 | Yang et al. |
| 5,866,336 A | 2/1999 | Nazarenko et al. |
| 5,939,265 A | 8/1999 | Cohen et al. |
| 5,989,823 A | 11/1999 | Jayasena et al. |
| 5,990,479 A | 11/1999 | Weiss et al. |
| 6,004,354 A | 12/1999 | Miller et al. |
| 6,071,726 A | 6/2000 | Diamandis et al. |
| 6,083,761 A | 7/2000 | Kedar et al. |
| 6,380,377 B1 | 4/2002 | Dattagupta |
| 6,500,622 B1 | 12/2002 | Bruchez et al. |
| 6,500,650 B1 | 12/2002 | Stanton, Jr. et al. |

Primary Examiner—Kenneth R. Horlick

(57) ABSTRACT

Methods, compositions and articles of manufacture for assaying a sample for a target polynucleotide and/or an amplification product therefrom are provided. The methods comprise contacting a sample suspected of containing the target polynucleotide with a polynucleotide that can bind specifically thereto; this polynucleotide is conjugated to a substrate, preferably an encoded bead conjugate. An amplification reaction can first be used to produce the amplification product from the target polynucleotide so that it can be used to indirectly assay for the target polynucleotide. An amplification product detection complex and method of forming the same are also provided. The methods are particularly useful in multiplex settings where a plurality of targets are present. Amplification product assay complexes and amplification product assay arrays are also provided, along with methods of forming the same. Kits comprising reagents for performing such methods are also provided.

4 Claims, 16 Drawing Sheets

Molecular Beacon on Spectrally Encoded Microspheres + Target Oligonucleotide

Molecular Beacons on Qbead Microspheres + Target Oligonucleotide

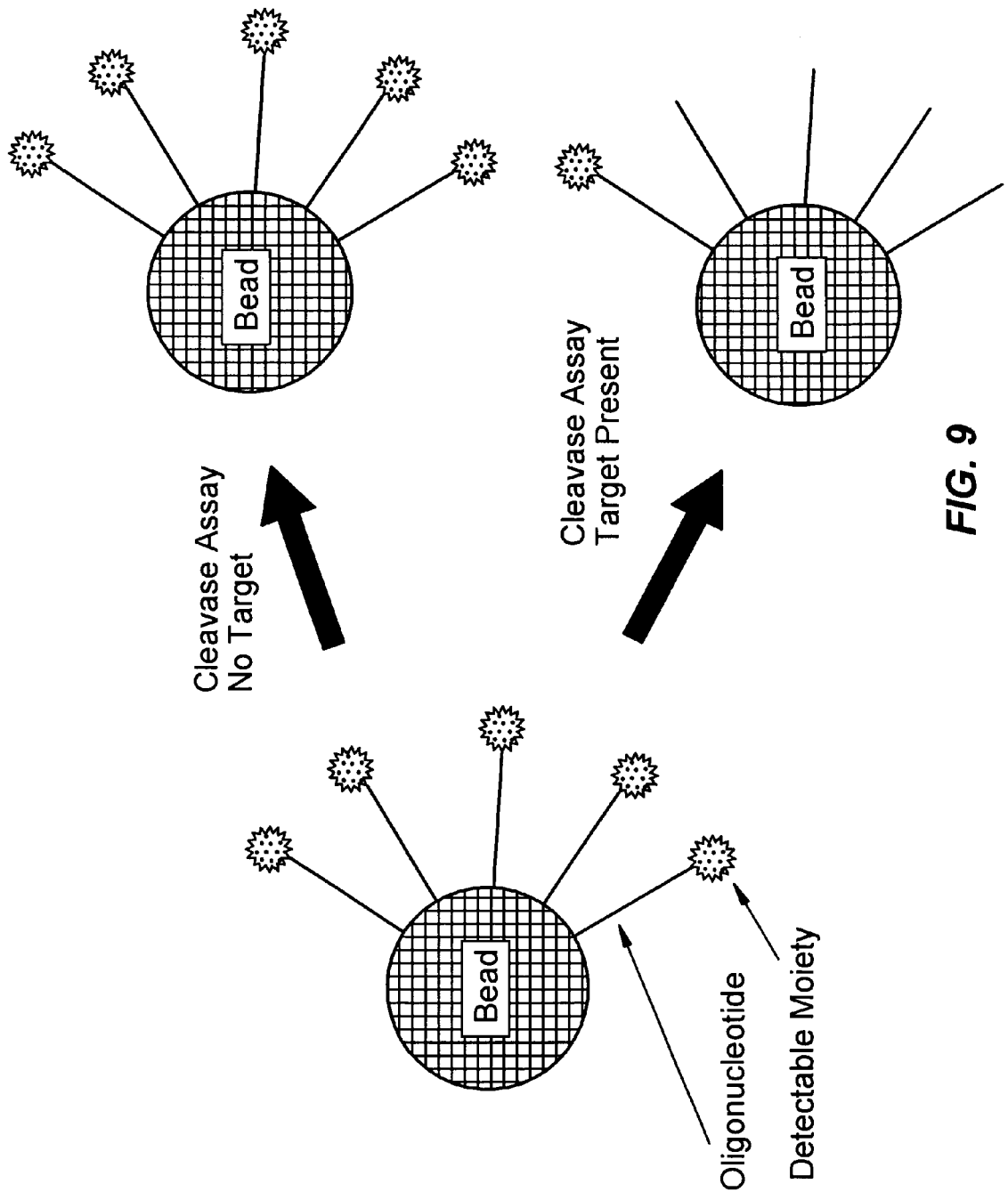

LOOP PROBE HYBRIDIZATION ASSAY FOR POLYNUCLEOTIDE ANALYSIS

CROSS-REFERENCE TO RELATED APPLICATIONS

This application is a continuation of U.S. patent application Ser. No. 09/815,510, filed Mar. 22, 2001, U.S. Pat. No. 6,653,080, from which application priority is claimed pursuant to 35 U.S.C. § 120, and claims the benefit of Provisional Patent Application No. 60/191,227, filed Mar. 22, 2000, and 60/237,000, filed Sep. 29, 2000, from which priority is claimed under 35 USC § 119(e)(1), and which applications are incorporated herein by reference in their entireties.

TECHNICAL FIELD

This invention relates to methods, articles and compositions for the analysis of polynucleotides in a sample.

BACKGROUND OF THE INVENTION

Michael Adams-Conroy died at the age of nine of the highest overdose of Prozac® on record, seven times higher than any previously known. His parents were investigated for homicide and his two siblings were removed from their custody by social welfare workers. Autopsy results, however, showed no pills in his stomach even though he would normally have had to ingest a huge number in order to reach the levels of drug found in his blood.

Acute lymphocytic leukemia (ALL) affects thousands of children each year in the United States. Treatment with chemotherapeutic agents now leads to remission in over 90% of the cases. 6-mercaptopurine (6-MP) is one agent used to treat ALL. However, the normal treatment dose of 6-MP is toxic for one in 300 patients and can kill rather than cure.

Adverse reactions to therapeutic drugs have been estimated to kill over 100,000 hospitalized patients in the U.S. each year (Lazarou et al., JAMA 1998 Apr. 15;279(15): 1200–5). This figure does not include intentional overdoses leading to hospitalization which ultimately prove fatal. An additional 2.2 million serious nonfatal adverse drug reactions have been estimated to occur.

The problem of the varied responses of individual patients to particular drug therapies is well known, but little progress has been made towards anticipating patients' varied drug metabolisms prior to treatment. The standard approach in administering drugs has been to prescribe the recommended dosage for a given condition to an affected patient, in some cases adjusting for the patient's weight. If the patient does not improve, the dosage is increased or an alternative drug is tried. Conversely, if adverse side effects occur, the dosage may be lowered or an alternative drug employed.

Drugs which exhibit serious side effects may never be approved by regulatory authorities or, if approved before such side effects are identified, can be withdrawn from the market if even a small percentage of treated patients are so affected. This can occur despite the fact that such drugs may have great therapeutic benefit in the majority of patients.

The 6-MP sensitivity exhibited by rare ALL patients has been linked to a deficiency in thiopurine S-methyltransferase (TPMT) activity (Krynetski et al., Pharm Res 1999 16(3): 342–9). Patients deficient in this enzyme can be treated with lower doses of 6-MP to achieve the same therapeutic plasma levels while avoiding adverse toxicity if the prescribing physician is aware of the metabolic deficiency. Metabolism of similar drugs such as azathioprine and thioguanine used in the treatment of rheumatoid arthritis, leukemia and Crohn's disease is also affected in patients who are deficient in TPMT.

Cytochrome p-450 CYP2D6 (debrisoquin hydroxylase) is the primary enzyme responsible for human metabolism of fluoxetine (Prozac®), as well as codeine, amphetamines, methadone, and several antidepressants and neuroleptics. At least twenty variants of the CYP2D6 gene are now known to result in poor metabolism of Prozac® and other drugs (Wong et al., Ann Acad Med Singapore 2000 29(3):401–6). Approximately 7–10% of Caucasians are poor metabolizers of Prozac®, and reach higher than expected plasma levels when treated with a standard dosage.

Michael Adams-Conroy was one such patient, but he was never tested to determine whether he harbored any of the CYP2D6 variants resulting in slow metabolism of Prozac. Instead, because of his diminished response to Prozac®, as typically occurs with chronic use, his dosage was gradually increased to maintain control over his symptoms. Side effects associated with Prozac® toxicity such as nausea and dizziness were instead attributed to migraines. Only after Michael's death were his tissues tested and shown to contain CYP2D6 variants which contributed to a toxic accumulation of Prozac® and its metabolites in his blood (Sallee et al., J. Child Adolesc. Psychopharmacol. 2000 Spring; 10(1):27–34).

Potentially fatal adverse drug reactions are now known to be associated with altered metabolism by patients harboring variants in a number of genes, including in the NAT2 gene affecting isoniazid metabolism, in the CYP2C9 gene affecting warfarin metabolism, in the DPD gene affecting 5-fluorouracil metabolism, and in the KCNE2 gene affecting clarithromycin metabolism (Grant et al., Pharmacology 2000 61(3):204–11; Taube et al., Blood 2000 96(5):1816–9; Meinsma et al., DNA Cell Bio 1995 14(1):1–6; Sesti et al., Proc Natl Acad Sci USA 2000 97(19):10613–8).

There is a need in the art for methods of analyzing samples for particular polynucleotides, and for devices, compositions and articles of manufacture useful in such methods.

SUMMARY OF THE INVENTION

Methods, compositions and articles for assaying a sample for a target polynucleotide or an amplification product therefrom are provided. The methods involve contacting a sample suspected of containing a target polynucleotide with an encoded bead conjugate comprising a probe polynucleotide and a spectral code comprising a semiconductor nanocrystal. The probe polynucleotide can be in a form suitable for performing a cleavase assay, or can be a molecular beacon, or can have an unlabeled stem-loop structure. Binding of the probe polynucleotide to the target polynucleotide results in a change in fluorescence characteristics of the encoded bead conjugate. Amplification reactions can be incorporated into the methods.

In one variation of the method, an unlabeled probe polynucleotide that can form a stem-loop structure is employed which can be conjugated to any form of substrate and used to assay for a labeled amplification product. Binding of the probe polynucleotide to the labeled amplification product unfolds the stem-loop structure and results in the production of an amplification product assay complex. Where a plurality of different unlabeled probe polynucleotides are attached to the substrate, binding of a plurality of corresponding different labeled amplification products results in the formation of an amplification product assay array.

Kits comprising reagents useful for performing the methods of the invention are also provided.

The methods are particularly useful in multiplex settings where a plurality of different conjugates are used to assay for a plurality of different target polynucleotides. The large number of distinguishable semiconductor nanocrystal labels allows for the simultaneous analysis of multiple labeled target polynucleotides, along with multiple different encoded bead conjugates.

Methods of the invention can optionally be implemented in a homogeneous format. This allows for higher assay throughput due to fewer manipulations of the sample, and decreased cross-contamination resulting in more reliable assays and less downtime from cross-contamination. If real time monitoring is used, the entire assay can be disposed of without opening a sealed assay chamber such as a sealed microplate, thus further decreasing the risk of cross-contamination.

BRIEF DESCRIPTION OF THE DRAWINGS

FIG. 9 shows one variation of the cleavase on a bead assay in which the oligonucleotide linked to the bead is initially labeled at its proximal end, and cleavage in the presence of target nucleic acid leads to a decrease in the label associated with the bead.

DETAILED DESCRIPTION OF THE INVENTION

Figure 1A:
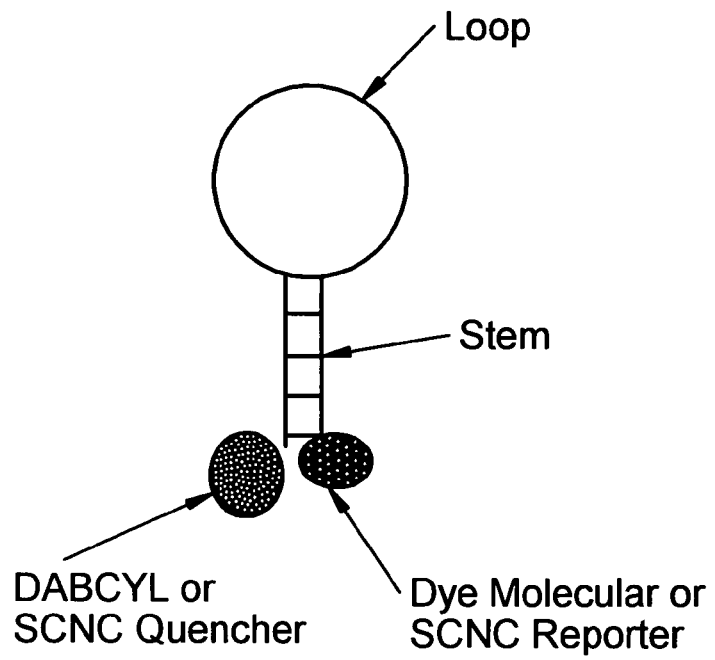
FIG. 1A depicts a molecular beacon comprising a polynucleotide having a hairpin or stem-loop structure, with a quencher located at one end of the polynucleotide and a fluorophore located at the opposite end of the polynucleotide, such that the quencher can quench a fluorescence emission from the fluorophore when the molecular beacon forms the stem-loop structure.

Gene variants are not only associated with adverse drug side effects. Variations in genes controlling patient drug response can also correlate with the inability of drugs to result in a successful therapeutic outcome. For example, Alzheimer's patients having the ApoE E4 subtype are less likely to benefit from the drug tacrine (PNAS 1995, 92:12260–4, Poirier et al.).

Inventions useful for assaying for particular polynucleotide sequences, whether based on SNPs, conserved sequences, or other features, have use in a wide variety of different applications. In addition to pharmacogenetic testing, such methods can be used in a forensic setting to identify the species or individual which was the source of a forensic specimen. Polynucleotide analysis methods can also be used in an anthropological setting. Paternity testing is another area in which such inventions can be used, as is testing for compatibility between prospective tissue or blood donors and patients in need thereof, and in screening for hereditary disorders.

The inventions can be used to study alterations of gene expression in response to a stimulus. Other applications include human population genetics, analyses of human evolutionary history, and characterization of human haplotype diversity.

The inventions can also be used; to detect immunoglobulin class switching and hypervariable mutation of immunoglobulins; to detect polynucleotide sequences from contaminants or pathogens including bacteria, yeast and viruses; for HIV subtyping to determine the particular strains or relative amounts of particular strains infecting an individual; and can be done repeatedly to monitor changes in the individuals predominant HIV strains, such as the development of drug resistance or T cell tropism; and to detect single nucleotide polymorphisms, which may be associated with particular alleles or subsets of alleles. Over 1.4 million different single nucleotide polymorphisms (SNPs) in the human population have been identified (Nature 2001 409: 928–933).

The inventions can be used for mini-sequencing, and for detection of mutations. Any type of mutation can be detected, including without limitation SNPs, insertions, deletions, transitions, transversions, inversions, frame shifts, triplet repeat expansion, and chromosome rearrangements. The invention can be used to detect nucleotide sequences associated with increased risk of diseases or disorders, including cystic fibrosis, Tay-Sachs, sickle-cell anemia, etc.

The inventions described herein can be used for any assay in which a sample is interrogated regarding a target polynucleotide or amplification product therefrom. Typical assays involve determining the presence of the target polynucleotide or amplification product therefrom in the sample or its relative amount, or can be quantitative or semi-quantitative. The invention provides an encoded bead conjugate comprising a first polynucleotide linked to a microsphere comprising a spectral code and having first fluorescence characteristics. The linkage may be direct or indirect, and can be linked at any point in the polynucleotide, so long as the conjugate can be used under assay conditions. The spectral code comprises a semiconductor nanocrystal, which can be incorporated into the microsphere or attached thereto, directly or indirectly. High density spectral coding schemes can be used.

Methods amenable to multiplexing, such as those taught herein, allow acquisition of greater amounts of information from smaller specimens. The need for smaller specimens increases the ability of an investigator to obtain samples from a larger number of individuals in a population to validate a new assay or simply to acquire data, as less invasive techniques are needed.

One or more different populations of spectrally encoded bead conjugates are created, each population comprising a known probe polynucleotide attached to a microsphere comprising a known or determinable spectral code comprising one or more semiconductor nanocrystals. Different populations of the conjugates, and thus different assays, can be blended together, and the assay can be performed in the presence of the blended populations. The individual conjugates are scanned for their spectral properties, which allows the spectral code to be decoded and thus identifies the bead, and therefore the polynucleotide to which it is attached.

Because of the large number of different semiconductor nanocrystals and mixtures thereof which can be distinguished, large numbers of different probe polynucleotides and target polynucleotides can be simultaneously interrogated. Multiplex methods are also provided employing 2, 3, 4, 5, 10, 15, 20, 25, 50, 100, 200, 500, 1000 or more different probe polynucleotides which can be used simultaneously with corresponding different target polynucleotides, for example in a microarray format or conjugated to microspheres spectrally encoded with SCNCs.

One method of the invention employs the encoded bead conjugate as a substrate on which an assay for a target polynucleotide in a sample is performed. The first polynucleotide can be labeled or unlabeled. Upon hybridization of the target polynucleotide to the first polynucleotide, at least a part of which is complementary to at least a part of the target polynucleotide or an amplification product therefrom, a change in the fluorescence characteristics of the conjugate occurs.

The first polynucleotide can be designed so that it can be used in a cleavase assay for the target polynucleotide. Binding of the first polynucleotide and an invader polynucleotide to the target polynucleotide in the presence of a flap endonuclease results in the cleavage of the first polynucleotide upon displacement by the invader polynucleotide of at least one nucleotide in the first polynucleotide that is complementary to the target polynucleotide. If the first polynucleotide was labeled with a fluorophore at a distal end, that label will be lost upon cleavage, resulting in a corresponding change in the fluorescence characteristics of the conjugate.

Conversely, if the first polynucleotide was originally unlabeled, cleavage by the flap endonuclease can expose a residue of the first polynucleotide that allows a fluorescent label to be incorporated, for example via ligation to a labeled polynucleotide or via the activity of terminal transferase or a polymerase in the presence of labeled nucleotides, thus resulting in a corresponding change in the fluorescence characteristics of the conjugate.

The first polynucleotide can also form a stem-loop structure. Where the first polynucleotide does not comprise a label, it can be conjugated to any substrate and used to bind to a corresponding labeled target polynucleotide that can bind to at least a part of the loop portion and thereby disrupt formation of the stem-loop. When this variation of the first polynucleotide is conjugated to an encoded bead, binding of a fluorescently labeled amplification product similarly results in a change in the fluorescence characteristics of the conjugate.

When the first polynucleotide comprises a stem-loop structure, the first polynucleotide can be in the form of a molecular beacon. In this variation, the conjugate comprises a quencher and a fluorophore, at least one of which is linked at or nearer the distal end of the first polynucleotide, directly or indirectly. The other of the quencher and fluorophore is linked at or nearer a proximal end of the first polynucleotide or on the surface of the bead, directly or indirectly. The quencher and the fluorophore in this arrangement are of a type and are located such that the fluorescence emission from the fluorophore is quenched when the stem-loop structure is formed, and the fluorescence emission from the fluorophore is not quenched when the first polynucleotide is hybridized to the target polynucleotide. In a variation, a self-quenching dye can be used that is both the fluorophore and quencher, and its location in the stem-loop structure can be varied as desired so that its fluorescence emission is either quenched or unquenched when the stem-loop structure is formed, with the converse occurring when the target polynucleotide is bound.

When the first polynucleotide is unlabeled and forms a stem-loop structure, it can be referred to as a probe polynucleotide and can be conjugated to any substrate to form an article of manufacture. Hybridization of a labeled amplification product to the first polynucleotide can then be detected by determining if the label is associated with the substrate; such hybridization forms an amplification product assay complex. A method of making such a complex via such hybridization is also provided. An amplification product assay array comprising a plurality of different probe polynucleotides having different sequences hybridized to corresponding different labeled amplification products is also provided.

The methods of the invention can all be performed in multiplex formats. A plurality of different first, or probe, polynucleotides which preferentially hybridize to corresponding different target polynucleotides, or amplification products therefrom, can be conjugated to the same substrate. The separate binding of each different amplification product to its corresponding first, or probe, polynucleotide can be detected by using a different label on each different amplification product, by the location on the substrate at which each probe polynucleotide is located, or by the conditions under which each amplification product binds, or combinations thereof.

One or more cycles of an amplification reaction can be incorporated into the methods to increase the copy number of the target polynucleotide and thereby increase sensitivity.

Before the present invention is described in detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a target" includes a plurality of targets, reference to "a substrate" includes a plurality of such substrates, reference to "a probe" includes a plurality of probes, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Definitions

In describing the present invention, the following terms will be employed, and are intended to be defined as indicated below.

The terms "semiconductor nanocrystal," "SCNC," "quantum dot" and "SCNC™ nanocrystal" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). SCNCs are characterized by their uniform nanometer size. An SCNC is capable of emitting electromagnetic radiation upon excitation (i.e., the SCNC is luminescent) and includes a "core" of one or more first semiconductor materials, and may be surrounded by a "shell" of a second semiconductor material. An SCNC core surrounded by a semiconductor shell is referred to as a "core/shell" SCNC. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the group II–VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III–V (GaN, GaP, GaAs, GaSb, InN, InP, InAs, InSb, and the like) and IV (Ge, Si, and the like) materials, PbSe, and an alloy or a mixture thereof. Preferred shell materials include CdS and ZnS.

An SCNC is optionally surrounded by a "coat" of an organic capping agent. The organic capping agent may be any number of materials, but has an affinity for the SCNC surface. In general, the capping agent can be an isolated organic molecule, a polymer (or a monomer for a polymerization reaction), an inorganic complex, or an extended crystalline structure. The coat can be used to convey solubility, e.g., the ability to disperse a coated SCNC homogeneously into a chosen solvent, functionality, binding properties, or the like. In addition, the coat can be used to tailor the optical properties of the SCNC.

Thus, the terms "semiconductor nanocrystal," "SCNC," "quantum dot" and "SCNC™ nanocrystal" as used herein include a coated SCNC core, as well as a core/shell SCNC.

"Monodisperse particles" include a population of particles wherein at least about 60% of the particles in the population, more preferably about 75 to about 90, or any integer therebetween, percent of the particles in the population fall within a specified particle size range. A population of monodisperse particles deviates less than 10% rms (root-mean-square) in diameter, and preferably deviates less than 5% rms.

The phrase "one or more sizes of SCNCs" is used synonymously with the phrase "one or more particle size distributions of SCNCs." One of ordinary skill in the art will realize that particular sizes of SCNCs are actually obtained as particle size distributions.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Afiti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base Which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'-H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489–10496 and references cited therein; 2'-deoxy-5-methylisocytidine may be prepared by the method of Tor et al. (1993) J. Am. Chem. Soc. 115:4461–4467 and references cited therein; and isoguanine nucleotides may be prepared using the method described by Switzer et al. (1993), supra, and Mantsch et al. (1993) Biochem. 14:5593–5601, or by the method described in U.S. Pat. No. 5,780,610 to Collins et al. Other nonnatural base pairs may be synthesized by the method described in Piccirilli et al. (1990) Nature 343: 33–37 for the synthesis of 2,6-diaminopyrimidine and its complement (1-methylpyrazolo-[4,3]pyrimidine-5,7-(4H, 6H)-dione. Other such modified nucleotidic units which form unique base pairs are known, such as those described in Leach et al. (1992) J. Am. Chem. Soc. 114:3675–3683 and Switzer et al., supra.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

"Complementary" or "substantially complementary" refers to the ability to hybridize or base pair between nucleotides or nucleic acids, such as, for instance, between the two strands of a double stranded DNA molecule or between a polynucleotide primer and a primer binding site on a single stranded nucleic acid to be sequenced or amplified. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984).

"Preferential binding" or "preferential hybridization" refers to the increased propensity of one polynucleotide to bind to a complementary target polynucleotide in a sample as compared to noncomplementary polynucleotides in the sample or as compared to the propensity of the one polynucleotide to form an internal secondary structure such as a hairpin or stem-loop structure under at least one set of hybridization conditions.

Stringent hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art. Less stringent, and/or more physiological, hybridization conditions are used where a labeled polynucleotide amplification product cycles on and off a substrate linked to a complementary probe polynucleotide during areal-time assay which is monitored during PCR amplification such as a molecular beacon assay. Such less stringent hybridization conditions can also comprise solution conditions effective for other aspects of the method, for example reverse transcription or PCR.

The terms "aptamer" (or "nucleic acid antibody") is used herein to refer to a single- or double-stranded polynucleotide that recognizes and binds to a desired target molecule by virtue of its shape. See, e.g., PCT Publication Nos. WO 92/14843, WO 91/19813, and WO 92/05285.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides contain [post-translational] modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

The terms "substrate" and "support" are used interchangeably and refer to a material having a rigid or semi-rigid surface.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof) IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

An "SCNC conjugate" is an SCNC linked to an oligonucleotide, as defined above.

An SCNC is "linked" or "conjugated" to, or chemically "associated" with, a polynucleotide when the SCNC is coupled to, or physically associated with the polynucleotide. Thus, these terms intend that the SCNC may either be directly linked to the polynucleotide or may be linked via a linker moiety, such as via a chemical linker. The terms indicate items that are physically linked by, for example, covalent chemical bonds, physical forces such van der Waals or hydrophobic interactions, encapsulation, embedding, or the like. For example, nanocrystals can be associated with biotin which can bind to the proteins avidin and streptavidin.

The term "antibody" as used herein includes antibodies obtained from both polyclonal and monoclonal preparations, as well as: hybrid (chimeric) antibody molecules (see, for example, Winter et al. (1991) *Nature* 349:293–299; and U.S. Pat. No. 4,816,567); F(ab')2 and F(ab) fragments; Fv molecules (noncovalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J Immunology* 149B:120–126); humanized antibody molecules (see, for example, Riechmann et al. (1988) *Nature* 332:323–327; Verhoeyan et al. (1988) *Science* 239:1534–1536; and U.K. Patent Publication No. GB 2,276,169, published 21 Sep. 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote, et al. *Monoclonal Antibodies and Cancer Therapy*, Alan R. Liss, 1985, p. 77.

A "homogeneous assay" is one that is performed without transfer, separation or washing steps. Thus, for example, a homogeneous high-throughput screening ("HTS") assay involves the initial addition of reagents to a vessel, e.g., a test tube or sample well, followed by the detection of the results from that vessel. A homogeneous HTS assay can be performed anywhere in the vessel, for example in the solution, on the surface of the vessel or on beads or surfaces placed in the vessel. The detection system typically used is a fluorescence, chemiluminescence, or scintillation detection system.

"Multiplexing" herein refers to an assay or other analytical method in which multiple probe polynucleotides can be assayed simultaneously by using more than one SCNC, each of which has at least one different fluorescence characteristic (for example excitation wavelength, emission wavelength, emission intensity, FWHM (full width at half maximum peak height), or fluorescence lifetime). Multiplexing also includes assays or methods in which the combination of more than one SCNC having distinct emission spectra can be used to detect a single probe polynucleotide.

For example, two different preparations of SCNCs may have the same composition but different particle sizes, and thus differ in excitation and/or emission wavelength. Or, two different preparations may have the same particle size or particle size distribution but different composition, and thus also differ in excitation and/or emission wavelength. Different preparations having different compositions of SCNCs can have different fluorescent lifetimes, and thus their emission spectra can be distinguished even when they have the same emission wavelength and intensity, for example by sampling the emission from the encoded substance at different times after excitation. Differences in FWHM can be achieved for example by using SCNCs of different composition, or of the same composition but which are synthesized differently, or by mixing different SCNC "preparations" having overlapping emission peaks together to form a new preparation.

A SCNC having a known emission wavelength and/or intensity may be included with the SCNCs conjugated to the polynucleotide defined herein to provide an internal standard for calibrating the wavelength and/or intensity of the other SCNC(s) used in the conjugate.

"Optional" or "optionally" means that the subsequently described event or circumstance may or may not occur, and that the description includes instances where the event or circumstance occurs and instances in which it does not. For example, the phrase "optionally surrounded by a 'coat' of an organic capping agent" with reference to an SCNC includes SCNCs having such a coat, and SCNCs lacking such a coat.

The Substrate

The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, or combinations thereof.

Substrates can be planar crystalline substrates such as silica based substrates (e.g. glass, quartz, or the like), or crystalline substrates used in, e.g., the semiconductor and microprocessor industries, such as silicon, gallium arsenide and the like.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, strand, precipitate, optionally porous gel, sheets, tube, sphere, container, capillary, pad, slice, film, chip, multiwell plate or dish, optical fiber, etc. Although typically the substrate takes an inanimate form, for some applications such as flow cytometry or in situ hybridization, the substrate can be any form that is rigid or semi-rigid, for example a cell, tissue, organism or nucleus, and may be optionally fixed. The substrate may contain raised or depressed regions on which a probe polynucleotide is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si—OH functionalities, such as those found on silica surfaces.

The substrate and/or its optional surface are chosen to provide appropriate optical characteristics for the synthetic and/or detection methods used. The substrate and/or surface can be transparent to allow the exposure of the substrate by light applied from multiple directions. The substrate and/or surface may be provided with reflective "mirror" structures to increase the recovery of light emitted by the semiconductor nanocrystal.

The substrate and/or its surface is generally resistant to, or is treated to resist, the conditions to which it is to be exposed in use, and can be optionally treated to remove any resistant material after exposure to such conditions.

Targets can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767–777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261.

Still further techniques include bead based techniques such as those described in PCT Appl. No. PCT/US93/04145 and pin based methods such as those described in U.S. Pat. No. 5,288,514.

Additional flow channel or spotting methods applicable to attachment of targets to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

A Microsphere Substrate

In a preferred embodiment, the substrate can be in the form of a microsphere. Polymeric microspheres or beads can be prepared from a variety of different polymers, including but not limited to polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers and epoxies. The materials have a variety of different properties with regard to swelling and porosity, which are well understood in the art. Preferably, the beads are in the size range of approximately 10 nm to 1 mm, and can be manipulated using normal solution techniques when suspended in a solution. The terms "bead", "sphere", "microbead" and "microsphere" are used interchangeably herein.

A plurality of such beads or mixtures of different bead populations can be immobilized on a planar surface such that they are regularly spaced in a chosen geometry using any suitable method. For example, beads can be immobilized by micromachining wells in which beads can be entrapped into the surface, or by patterned activation of polymers on the surface using light activation to cross-link single beads at particular locations. Suitable wells can be created by ablating circles in a layer of parylene deposited on a glass surface using a focused laser. The well dimensions are chosen such that a single bead can be captured per well and remain trapped when a lateral flow of fluid passes across the surface. For example, 7 micron wells can be readily used for analysis of beads about 4 microns to about 6 microns in diameter. This can be performed on the end of an optical fiber.

Spectrally Encoded Microspheres

Microspheres can be spectrally encoded through incorporation of SCNCs. The desired fluorescence characteristics of the microspheres may be obtained by mixing SCNCs of different sizes and/or compositions in a fixed amount and ratio to obtain the desired spectrum, which can be determined prior to association with the microspheres. Subsequent treatment of the microspheres (through for example covalent attachment, co-polymerization, or passive absorption or adsorption) with the staining solution results in a material having the designed fluorescence characteristics.

A number of SCNC solutions can be prepared, each having a distinct distribution of sizes and compositions, to achieve the desired fluorescence characteristics. These solutions may be mixed in fixed proportions to arrive at a spectrum having the predetermined ratios and intensities of emission from the distinct SCNCs suspended in that solution. Upon exposure of this solution to a light source, the emission spectrum can be measured by techniques that are well established in the art. If the spectrum is not the desired spectrum, then more of the SCNC solution needed to achieve the desired spectrum can be added and the solution "titrated" to have the correct emission spectrum. These solutions may be colloidal solutions of SCNCs dispersed in a solvent, or they may be pre-polymeric colloidal solutions, which can be polymerized to form a matrix with SCNCs contained within.

The composition of the staining solution can be adjusted to have the desired fluorescence characteristics, preferably under the exact excitation source that will be used for the decoding. A multichannel auto-pipettor connected to a feedback circuit can be used to prepare an SCNC solution having the desired spectral characteristics, as described above. If the several channels of the titrator/pipettor are charged with several unique solutions of SCNCs, each having a unique excitation and emission spectrum, then these can be combined stepwise through addition of stock solutions.

Once the staining solution has been prepared, it can be used to incorporate a unique spectral code into a given bead population. If the method of incorporation of the SCNCs into the beads is absorption or adsorption, then the solvent that is used for the staining solution should be one that is suitable for swelling the microspheres, and can be selected based on the microsphere composition. Typical solvents for swelling microspheres include those in which the microsphere material is more soluble, for example dichloromethane, chloroform, dimethylformamide, tetrahydrofuran and the like. These can be mixed with a solvent in which the microsphere material is less soluble, for example methanol or ethanol, to control the degree and rate of incorporation of the staining solution into the material.

The microspheres swell when added to the staining solution and incorporate a plurality of SCNCs in the relative proportions that are present in the staining solution. After removal of the staining solution from the material, a non-swelling solvent is added, the material shrinks, or unswells, thereby trapping the SCNCs in the material. Alternatively, SCNCs can be trapped by evaporation of the swelling solvent from the material. After rinsing with a nonswelling solvent in which the SCNCs can be suspended, the SCNCs are trapped in the material, and can be retained by further use of a nonswelling solvent. Typical nonswelling solvents include hexane and toluene. The thus-encoded beads can be separated and exposed to a variety of solvents without a change in the emission spectrum under the light source. When the material used is a polymer bead, the material can be separated from the rinsing solvent by any suitable technique, for example, centrifugation, evaporation, fluidized bed drying, etc., or combined procedures, and can be redispersed into aqueous solvents and buffers through the use of detergents in the suspending buffer.

The staining procedure can also be carried out in sequential steps. A first staining solution can be used to stain the beads with one population of SCNCs. The beads can then be separated from the first staining solution and added to a second staining solution to stain the beads with a second population of SCNCs. These steps can be repeated until the desired spectral properties are obtained from the material when excited by a light source.

The SCNCs can be attached to the beads by covalent attachment as well as by entrapment in swelled beads, or can be coupled to one member of a binding pair the other member of which is attached to the beads. For instance, SCNCs are prepared by a number of techniques that result in reactive groups on the surface of the SCNC. See, e.g., Bruchez et al. (1998) *Science* 281:2013–2016, Chan et al. (1998) *Science* 281:2016–2018, Colvin et al. (1992) *J. Am. Chem. Soc.* 114:5221–5230, Katari et al. (1994) *J. Phys. Chem.* 98:4109–4117, Steigerwald et al. (1987) *J. Am. Chem. Soc.* 110:3046. The reactive groups present on the surface of the SCNCs can be coupled to reactive groups present on a surface of the material. For example, SCNCs which have carboxylate groups present on their surface can be coupled to beads with amine groups using a carbodiimide activation step.

Any cross-linking method that links a SCNC to a bead and does not adversely affect the properties of the SCNC or the bead can be used. In a cross-linking approach, the relative amounts of the different SCNCs can be used to control the relative intensities, while the absolute intensities can be controlled by adjusting the reaction time to control the number of reacted sites in total. After the beads are crosslinked to the SCNCs, the beads are optionally rinsed to wash away unreacted SCNCs.

A sufficient amount of fluorophore must be used to encode the beads so that the intensity of the emission from the fluorophores can be detected by the detection system used and the different intensity levels must be distinguishable, where intensity is used in the coding scheme but the fluorescence emission from the SCNCs or other fluorophores used to encode the beads must not be so intense to as to saturate the detector used in the decoding scheme.

The Coding Scheme

The beads or other substrate to which one or more different known capture probes are conjugated can be encoded to allow rapid analysis of bead, and thus capture probe, identity, as well as allowing multiplexing. The coding scheme preferably employs one or more different SCNCs, although a variety of additional agents, including chromophores, fluorophores and dyes, and combinations thereof can be used alternatively or in combination with SCNCs. For organic dyes, different dyes that have distinguishable fluorescence characteristics can be used. Different SCNC populations having the same peak emission wavelength but different peak widths can be used to create different codes if sufficient spectral data can-be gathered to allow the populations to be distinguished. Such different populations can also be mixed to create intermediate linewidths and hence more unique codes.

The number of SCNCs used to encode a single bead or substrate locale can be selected based on the particular application. Single SCNCs can be detected; however, a plurality of SCNCs from a given population is preferably incorporated in a single bead to provide a stronger, more continuous emission signal from each bead and thus allow shorter analysis time.

Different SCNC populations can be prepared with peak wavelengths separated by approximately 1 nm, and the peak wavelength of an individual SCNC can be readily determined with 1 run accuracy. In the case of a single-peak spectral code, each wavelength is a different code. For example, CdSe SCNCs have a range of emission wavelengths of approximately 490–640 nm and thus can be used to generate about 150 single-peak codes at 1 nm resolution.

A spectral coding system that uses only highly separated spectral peaks having minimal spectral overlap and does not require stringent intensity regulation within the peaks allows for approximately 100,000 to 10,000,000 or more unique codes in different schemes.

A binary coding scheme combining a first SCNC population having an emission wavelength within a 490–565 nm channel and a second SCNC population within a 575–650 nm channel produces 3000 valid codes using 1-nm resolved SCNC populations if a minimum peak separation of 75 nm is used. The system can be expanded to include many peaks, the only requirement being that the minimum separation between peak wavelengths in valid codes is sufficient to allow their resolution by the detection methods used in that application.

A binary code using a spectral bandwidth of 300 nm, a coding-peak resolution, i.e., the minimum step size for a peak within a single channel, of 4 run, a minimum interpeak spacing of 50 nm, and a maximum of 6 peaks in each code results in approximately 200,000 different codes. This assumes a purely binary code, in which the peak within each channel is either "on" or "off." By adding a second "on" intensity, i.e., wherein intensity is 0, 1 or 2, the number of potential codes increases to approximately 5 million. If the coding-peak resolution is reduced to 1 run, the number of codes increases to approximately $1 \times 10^{10}$.

Valid codes within a given coding scheme can be identified using an algorithm. Potential codes are represented as a binary code, with the number of digits in the code corresponding to the total number of different SCNC populations having different peak wavelengths used for the coding scheme. For example, a 16-bit code could represent 16 different SCNC populations having peak emission wavelengths from 500 nm through 575 nm, at 5 nm spacing. A binary code 1000 0000 0000 0001 in this scheme represents the presence of the 500 nm and 575 nm peaks. Each of these 16-bit numbers can be evaluated for validity, depending on the spacing that is required between adjacent peaks; for example, 0010 0100 0000 0000 is a valid code if peaks spaced by 15 nm or greater can be resolved, but is not valid if the minimum spacing between adjacent peaks must be 20 nm. Using a 16-bit code with 500 to 575 nm range and 5 nm spacing between peaks, the different number of possible valid codes for different minimum spectral spacings between adjacent peaks is shown in Table 1.

TABLE 1

The number of unique codes with a binary 16-bit system.

| | Spectral Separation | | | | | |
|---|---|---|---|---|---|---|
| | 5 nm | 10 nm | 15 nm | 20 nm | 25 nm | 30 nm |
| Number of unique codes | 65535 | 2583 | 594 | 249 | 139 | 91 |

If different distinguishable intensities are used, then the number of valid codes dramatically increases. For example, using the 16-bit code above, with 15 nm minimum spacing between adjacent peaks in a code, 7,372 different valid codes are possible if two intensities, i.e., a ternary system, are used for each peak, and 38,154 different valid codes are possible for a quaternary system, i.e., wherein three "on" intensities can be distinguished.

Codes utilizing intensities require either precise matching of excitation sources or incorporation of an internal intensity standard into the beads due to the variation in extinction coefficient exhibited by individual SCNCs when excited by different wavelengths.

It is preferred that the light source used for the encoding procedure be as similar as possible (preferably of the same wavelength and intensity) to the light source that will be used for decoding. The light source may be related in a quantitative manner, so that the emission spectrum of the final material may be deduced from the spectrum of the staining solution.

The Encoded Bead Conjugate

The encoded bead conjugate comprises a first polynucleotide conjugated to a first microsphere comprising a first spectral code comprising a first semiconductor nanocrystal having first fluorescence characteristics.

The first polynucleotide can be synthesized directly on the substrate, or can be synthesized separately from the substrate and then coupled to it. Direct synthesis on the substrate may be accomplished by incorporating a monomer that is coupled to a subunit of the probe polynucleotide into a polymer that makes up or is deposited on or coupled to the substrate, and then synthesizing the remainder of the probe polynucleotide onto that subunit. Or the substrate or its coating may include or be derivatized to include a functional group which can be coupled to a subunit of the probe polynucleotide for synthesis, or may be coupled directly to the complete capture probe. Suitable coupling techniques are known in the art.

The first polynucleotide can be labeled or unlabeled. Upon hybridization of the target polynucleotide to the first polynucleotide, at least a part of which is complementary to at least a part of the target polynucleotide or an amplification product therefrom, a change in the fluorescence characteristics of the conjugate occurs.

The first polynucleotide can be designed so that it can be used in a cleavase assay for the target polynucleotide. The first polynucleotide thus must have a 3' region that is complementary to the target polynucleotide, and a 5' region that is not complementary to the target polynucleotide, but can be attached to the encoded bead in any orientation. An invader polynucleotide is also used which comprises a region that is complementary to the target polynucleotide and overlapping with the complementary region of the first polynucleotide. The invader polynucleotide has a higher melting temperature to the target polynucleotide than does the first polynucleotide, such that the invader polynucleotide will displace at least one base from the 5' end of the 3' complementary region of the first polynucleotide and thereby allow it to be cleaved by a flap endonuclease. Binding of the first polynucleotide and an invader polynucleotide to the target polynucleotide in the presence of a flap endonuclease results in the cleavage of the first polynucleotide upon displacement by the invader polynucleotide of at least one nucleotide in the first polynucleotide that is complementary to the target polynucleotide. If the first polynucleotide was labeled, for example with a fluorophore, at a distal end, that label will be lost upon cleavage, resulting in a corresponding change in the fluorescence characteristics of the conjugate. Conversely, if the first polynucleotide was originally unlabeled, cleavage by the flap endonuclease can expose a residue of the first polynucleotide that allows a fluorescent label to be incorporated, for example via ligation to a labeled polynucleotide or via the activity of terminal transferase or a polymerase in the presence of labeled nucleotides, thus resulting in a corresponding change in the fluorescence characteristics of the conjugate. A "rolling circle" type template can be used where a polymerase is used to extend from the exposed end of the cleaved first polynucleotide which can then hybridize to the template. An "invader-squared" format can be used in which the invader polynucleotide is itself produced by a cleavase reaction involving a different target polynucleotide, allowing the signal from that different target polynucleotide to be amplified. Additional rounds of such amplification are possible.

The first polynucleotide can also form a stem-loop structure. Typically the stem region will contain about 4–7 nucleotides, but the critical factor is that the first polynucleotide forms the stem-loop structure under the desired assay conditions in the absence of target polynucleotide; suitable assay conditions can be predicted using computer programs and the useful assay condition range can be empirically determined. Similarly, the loop region is typically in the range of about 15 nucleotides or more, typically ~15–18 nucleotides, but again the critical factor is that the target polynucleotide and/or amplification product can bind to at least a part of the loop region and thereby disrupt the stem-loop structure.

Where the first polynucleotide can form a stem-loop structure and does not comprise a label, it can be referred to as a probe polynucleotide and can be conjugated to any substrate to form an article of manufacture. The probe polynucleotide can be used to bind to a corresponding labeled amplification product from a target polynucleotide by hybridizing to at least a part of the loop portion of the loop probe and thereby disrupt formation of the stem-loop. Hybridization of a labeled amplification product to the first polynucleotide can then be detected by determining if the label is associated with the substrate; such hybridization forms an amplification product assay complex. An amplification product assay array comprising a plurality of different probe polynucleotides having different sequences hybridized to corresponding different labeled amplification products can also be prepared. When the probe polynucleotide is conjugated to an encoded bead, binding of a fluorescently labeled amplification product results in a change in the fluorescence characteristics of the conjugate.

The Stem-Loop Structure

The first or probe polynucleotide can form a stem-loop structure wherein first and second complementary sequences hybridize to each other to form a stem and a third sequence located therebetween forms a loop under at least one set of hybridization conditions. The third sequence is designed so that at least part of it is complementary to at least a part of the amplification product, such that upon hybridization of the probe polynucleotide to the amplification product, the stem-loop structure unfolds. The part of the probe polynucleotide that is complementary to the amplification product can additionally comprise part of either or both the first and second complementary sequences, or can be located entirely within the loop sequence, and can be the entire loop sequence or only a portion of it. The part of the probe polynucleotide that is complementary to the amplification product can be complementary to all or part of the amplification product. The only requirement for the probe polynucleotide is that the stem-loop structure is formed under at least one set of hybridization conditions, but the probe polynucleotide preferentially hybridizes to the amplification product rather than form the stem-loop structure under at least one set of hybridization conditions which occurs at some point during the assay being performed.

The Molecular Beacon

When the first polynucleotide comprises a stem-loop structure, the first polynucleotide can be in the form of a molecular beacon. In this variation, the conjugate comprises a quencher and a fluorophore, at least one of which is linked at or nearer the distal end of the first polynucleotide, directly or indirectly. The other of the quencher and fluorophore is linked at or nearer a proximal end of the first polynucleotide or on the surface of the bead, directly or indirectly. The quencher and the fluorophore in this arrangement are of a type and are located such that the fluorescence emission from the fluorophore is quenched when the stem-loop structure is formed, and the fluorescence emission from the fluorophore is not quenched when the first polynucleotide is hybridized to the target polynucleotide. In a variation, a self-quenching dye can be used that is both the fluorophore and quencher, and its location in the stem-loop structure can be varied as desired so that its fluorescence emission is either quenched or unquenched when the stem-loop structure is formed, with the converse occurring when the target polynucleotide is bound.

Alternatively, a quenchable dye can be used that eliminates the need for a separate quencher in a molecular beacon (PCT Publ. No. WO 99/11813, published Mar. 11, 1999). The quenchable dye fluorescence can be essentially completely quenched when the nucleotide to which it is attached is part of a duplex (e.g., BODIPY). Depending on whether the quenchable dye is located in the stem or the loop region of the stem-loop structure, it may be quenched or unquenched either when bound to its target polynucleotide or when bound to the amplification product.

The Sample

The portion of the sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample can also comprise a polynucleotide prepared through synthetic means, in whole or in part. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be a positive control sample which is known to contain the target polynucleotide. A negative control sample can also be used which, although not expected to contain the target polynucleotide, is suspected of containing it, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

The Target Polynucleotide and Amplification Products Produced Therefrom

The target polynucleotide can be single-stranded, double-stranded, or higher order, and can be linear or circular. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids. The target polynucleotide can be prepared synthetically or purified from a biological source. The target polynucleotide may be purified to remove or diminish one or more undesired components of the sample or to concentrate the target polynucleotide. Conversely, where the target polynucleotide is too concentrated for the particular assay, the target polynucleotide may be diluted.

Following sample collection and optional nucleic acid extraction, the nucleic acid portion of the sample comprising the target polynucleotide can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest and can be used to incorporate a label into an amplification product produced from the target polynucleotide using a labeled primer or labeled nucleotide. A variety of amplification methods are suitable for use, including the polymerase chain reaction method or (PCR), the ligase chain reaction (LCR), self sustained sequence replication (3SR), nucleic acid sequence-based amplification (NASBA), the use of Q Beta replicase, reverse transcription, nick translation, and the like, particularly where a labeled amplification product can be produced and utilized in the methods taught herein.

Where the target polynucleotide is single-stranded, the first cycle of amplification forms a primer extension product complementary to the target polynucleotide. If the target polynucleotide is single-stranded RNA, a polymerase with reverse transcriptase is used in the first amplification to reverse transcribe the RNA to DNA, and additional amplification cycles can be performed to copy the primer extension products. Where the target polynucleotide is double-stranded and two primers are used, both primer extension products are produced during the first amplification cycle. However, only the primer extension product that can bind to the polynucleotide attached to the substrate produces a detectable result. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to form that complementary template strand.

The target polynucleotide is typically amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity which can copy the target polynucleotide can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H-MMLV (SuperScript®), SuperScript® II, ThermoScript®, HIV-1, and RAV2 reverse transcriptases. All of these enzymes are commercially available. Exemplary polymerases with multiple specificities include RAV2, and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions, optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different regions of a particular polynucleotide within the sample.

Amplified target polynucleotides may be subjected to post amplification treatments. For example, in some cases, it may be desirable to fragment the target polynucleotide prior to hybridization with a polynucleotide array, in order to provide segments which are more readily accessible to the target polynucleotides and which avoid looping and/or hybridization to multiple probes. Fragmentation of the nucleic acids can be carried out by any method producing fragments of a size useful in the assay being performed; suitable physical, chemical and enzymatic methods are known in the art.

An amplification reaction can be performed under conditions which allow the probe polynucleotide to hybridize to the amplification product during at least part of an amplification cycle. When the assay is performed in this manner, real-time detection of this hybridization event can take place by monitoring for a change in fluorescence properties of the substrate that occurs upon such hybridization during the amplification. Alternatively, the amplification reaction may occur under conditions which do not allow such binding during cycling, for example elevated temperature or in the absence of the probe polynucleotide, and the condition of the sample must be altered to allow detection to take place, for example by lowering the temperature or by contacting the sample with the first or probe polynucleotide. The stem-loop structure can be designed with the amplification reaction conditions in mind to either hybridize during an amplification cycle or not.

Labels

Labels useful in the inventions described herein include any substance which can be detected in association with the substrate when the molecule to which the label is attached, directly or indirectly, is hybridized to a polynucleotide which is attached to the substrate. Any effective detection method can be used, including optical, spectroscopic, electrical, piezoelectrical, magnetic, Raman scattering, surface plasmon resonance, radiographic, colorimetric, calorimetric, etc.

The label comprises an agent selected from a chromophore, a lumiphore, a fluorophore, a chromogen, a hapten, an antigen, a radioactive isotope, a magnetic particle, a metal nanoparticle such as a gold or silver nanoparticle, an enzyme, an antibody or binding portion or equivalent thereof, an aptamer, and one member of a binding pair.

A fluorophore can be any substance which absorbs light of one wavelength and emits light of a different wavelength. Typical fluorophores include fluorescent dyes, semiconductor nanocrystals, lanthanide chelates, and a green fluorescent protein.

Exemplary semiconductor nanocrystals include those SCNCs described above. Exemplary fluorescent dyes include fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy2, JOE, NED, ROX, HEX, Lucifer Yellow, Oregon Green 488, Oregon Green 500, Oregon Green 514, 7-amino-4-methylcoumarin-3-acetic acid, BODIPY FL, BODIPY FL- Br$_2$, BODIPY 530/550, BODIPY 558/568, BODIPY 564/570, BODIPY 576/589, BODIPY 581/591, BODIPY 630/650, BODIPY 650/665, BODIPY R6G, BODIPY TMR and BODIPY TR. Exemplary lanthanide chelates include europium chelates, terbium chelates and samarium chelates.

The term "green fluorescent protein" refers to both native and mutated versions of Aequorea green fluorescent protein that have been identified as exhibiting altered fluorescence characteristics, including altered excitation and emission maxima, as well as excitation and emission spectra of different shapes (Delagrave, S. et al. (1995) Bio/Technology 13:151–154; Heim, R. et al. (1994) Proc. Natl. Acad. Sci. USA 91:12501–12504; Heim, R. et al. (1995) Nature 373: 663–664). Delgrave et al. isolated mutants of cloned Aequorea victoria GFP that had red-shifted excitation spectra. Bio/Technology 13:151–154 (1995). Heim, R. et al. reported a mutant (Tyr66 to His) having ablue fluorescence (Proc. Natl. Acad. Sci. (1994) USA 91:12501–12504).

Exemplary enzymes include alkaline phosphatase, horseradish peroxidase, β-galactosidase, glucose oxidase, a bacterial luciferase, an insect luciferase and sea pansy luciferase (*Renilla koellikeri*), which can create a detectable signal in the presence of suitable substrates and assay conditions, known in the art.

Exemplary haptens and/or members of a binding pair include avidin, streptavidin, digoxigenin, biotin, and those described above.

The Quencher

The quencher can be any material that can quench at least one fluorescence emission from an excited fluorophore being used in the assay. A number of suitable quenchers are known in the art and are commercially available. Typical quenchers include DABCYL, BHQ-1, BHQ-2, BHQ-3, a metal nanoparticle, and a semiconductor nanocrystal having a broad absorbance spectra and an emission wavelength outside the range being detected in the current assay, or a semiconductor nanocrystal having no detectable emission.

Production of SCNCs

SCNCs for use in the subject methods can be made from any material and by any technique that produces SCNCs having emission characteristics useful in the methods, articles and compositions taught herein. The SCNCs have absorption and emission spectra that depend on their size, size distribution and composition. Suitable methods of production are disclosed in U.S. Pats. Nos. 6,048,616; 5,990,479; 5,690,807; 5,505,928; 5,262,357; PCT Publication No. WO 99/26299 (published May 27, 1999; inventors Bawendi et al.); Murray et al. (1993) J. Am. Chem. Soc. 115: 8706–8715; and Guzelian et al. (1996) J. Phys. Chem. 100:7212–7219.

Examples of materials from which SCNCs can be formed include group II–VI, III–V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge, Si, and ternary and quaternary mixtures thereof.

The composition, size and size distribution of the semiconductor nanocrystal affect its absorption and emission spectra. Exemplary SCNCs that emit energy in the visible range include CdS, CdSe, CdTe, ZnSe, ZnTe, GaP, and GaAs. Exemplary SCNCs that emit energy in the near IR range include InP, InAs, InSb, PbS, and PbSe. Exemplary SCNCs that emit energy in the blue to near-ultraviolet include ZnS and GaN. The size of SCNCs in a given population can be determined by the synthetic scheme used and/or through use of separation schemes, including for example size-selective precipitation and/or centrifugation. The separation schemes can be employed at an intermediate step in the synthetic scheme or after synthesis has been completed. For a given composition, larger SCNCs absorb and emit light at longer wavelengths than smaller SCNCs. SCNCs absorb strongly in the visible and UV and can be excited efficiently at wavelengths shorter than their emission peak. This characteristic allows the use in a mixed population of SCNCs of a single excitation source to excite all the SCNCs if the source has a shorter wavelength than the shortest SCNC emission wavelength within the mixture; it also confers the ability to selectively excite subpopulation(s) of SCNCs within the mixture by judicious choice of excitation wavelength.

The surface of the SCNC is preferably modified to enhance emission efficiency by adding an overcoating layer to form a "shell" around the "core" SCNC, because defects in the surface of the core SCNC can trap electrons or holes and degrade its electrical and optical properties. Addition of an insulating shell layer removes nonradiative relaxation pathways from the excited core, resulting in higher luminescence efficiency. Suitable materials for the shell include semiconductor materials having a higher bandgap energy than the core and preferably also having good conductance and valence band offset. Thus, the conductance band of the shell is desirably of a higher energy and the valence band is desirably of a lower energy than those of the core. For SCNC cores that emit energy in the visible (e.g., CdS, CdSe, CdTe, ZnSe, ZnTe, GaP, GaAs) or near IR (e.g., InP, InAs, InSb, PbS, PbSe), a material that has a bandgap energy in the ultraviolet may be used for the shell, for example ZnS, GaN, and magnesium chalcogenides, e.g., MgS, MgSe, and MgTe. For an SCNC core that emits in the near IR, materials having a bandgap energy in the visible, such as CdS or CdSe, or the ultraviolet may be used. Preparation of core-shell SCNCs is described in, e.g., Dabbousi et al. (1997) J. Phys. Chem. B 101:9463; Kuno et al., J. Phys. Chem. 106:9869 (1997); Hines et al., J. Phys. Chem. 100:468; and PCT Publ. No. WO 99/26299. The SCNCs can be made further luminescent through overcoating procedures as described in Danek et al. (1996) Chem. Mat. 8(1):173–180, and Peng et al. (1997) J. Am. Chem. Soc. 119:7019–7029.

Most SCNCs are typically prepared in coordinating solvent, such as TOPO and trioctyl phosphine (TOP), resulting in the formation of a passivating organic layer on the surface of SCNCs with and without a shell. Such passivated SCNCs can be readily solubilized in organic solvents, for example toluene, chloroform and hexane. Molecules in the passivating layer can be displaced or modified to provide an outermost coating that adapts the SCNCs for use in other solvent systems, for example aqueous systems.

Alternatively, an outermost layer of an inorganic material such as silica can be added around the shell to improve the aqueous dispersibility of the SCNCs, and the surface of the silica can optionally be derivatized (Bruchez et al., Science 281:2013 (1998)).

A displacement reaction may also be employed to modify the SCNC to improve the solubility in a particular organic solvent. For example, if it is desired to associate the SCNCs with a particular solvent or liquid, such as pyridine, the surface can be specifically modified with pyridine or pyridine-like moieties which are soluble or miscible with pyridine to ensure solvation. Water-dispersible SCNCs can be prepared as described in Bawendi et al., PCT Publ. No. WO 00/17655, published Mar. 30, 2000.

The surface layer of the SCNCs may be modified by displacement to render the SCNC reactive for a particular coupling-reaction. For example, displacement of trioctylphosphine oxide (TOPO) moieties with a group containing a carboxylic acid moiety enables the reaction of the modified SCNCs with amine containing moieties to provide an amide linkage. For a detailed description of these linking reactions, see, e.g., U.S. Pat. No. 5,990,479; Bruchez et al. (1998) *Science* 281:2013–2016, Chan et al. (1998) *Science* 281:2016–2018, Bruchez "Luminescent SCNCs: Intermittent Behavior and use as Fluorescent Biological Probes" (1998) Doctoral dissertation, University of California, Berkeley, and Mikulec "SCNC Colloids: Manganese Doped Cadmium Selenide, (Core) Shell Composites for Biological Labeling, and Highly Fluorescent Cadmium Telluride" (1999) Doctoral dissertation, Massachusetts Institute of Technology. The SCNC may be conjugated to other moieties directly or indirectly through a linker.

Examples of suitable spacers or linkers are polyethyleneglycols, dicarboxylic acids, polyamines and alkylenes. The spacers or linkers are optionally substituted with functional groups, for example hydrophilic groups such as amines, carboxylic acids and alcohols or lower alkoxy group such as methoxy and ethoxy groups. Additionally, the spacers will have an active site on or near a distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., Solid Phase Peptide Synthesis, IRL Press (1989).

The Excitation Source

By exposing the encoded beads or other substrate prepared and described as above to light of an excitation source, the SCNCs disposed in the material will be excited to emit light. This excitation source is of an energy capable of exciting at least one population of SCNCs used in the experiment to emit light and preferably chosen to be of higher energy than the shortest emission wavelength of the SCNCs used. Further, the excitation source is can be chosen such that it excites a minimum number of SCNCs in the sample to produce detectable light. Preferably the excitation source will excite a sufficient number of different populations of SCNCs to allow unique identification of all the encoded materials used in the experiment. For example, using two different populations of beads having different ratios of red to blue SCNCs, it would not be sufficient to only excite the red emitting SCNCs, e.g., by using green or yellow light, of the sample in order to decode the beads. It would be necessary to use a light source comprising at least one wavelength that is capable of exciting the blue emitting and the red emitting SCNCs simultaneously, e.g., violet or ultraviolet. There may be one or more light sources used to excite the different populations of SCNCs simultaneously, or sequentially, but a given light source will only excite subpopulations of SCNCs that emit at lower energy than the light source, due to the absorbance spectra of the SCNCs.

In addition, if a lamp source is used, degradation of the lamp can result in changes in the excitation source, thereby compromising the codes.

Detection of SCNC Emission

An example of an imaging system for automated detection for use with the present methods comprises an excitation source, a monochromator (or any device capable of spectrally resolving the image, or a set of narrow band filters) and a detector array. The excitation source can comprise blue or UV wavelengths shorter than the emission wavelength(s) to be detected. This may be: a broadband UV light source, such as a deuterium lamp with a filter in front; the output of a white light source such as a xenon lamp or a deuterium lamp after passing through a monochromator to extract out the desired wavelengths; or any of a number of continuous wave (cw) gas lasers, including but not limited to any of the Argon Ion laser lines (457, 488, 514, etc. nm) or a HeCd laser; solid state diode lasers in the blue such as GaN and GaAs (doubled) based lasers or the doubled or tripled output of YAG or YLF based lasers; or any of the pulsed lasers with output in the blue.

The emitted light can be detected with a device that provides spectral information for the substrate, e.g., grating spectrometer, prism spectrometer, imaging spectrometer, or the like, or use of interference (bandpass) filters. Using a two-dimensional area imager such as a CCD camera, many objects may be imaged simultaneously. Spectral information can be generated by collecting more than one image via different bandpass, longpass, or shortpass filters (interference filters, or electronically tunable filters are appropriate). More than one imager may be used to gather data simultaneously through dedicated filters, or the filter may be changed in front of a single imager. Imaging based systems, like the Biometric Imaging system, scan a surface to find fluorescent signals.

A scanning system can be used in which the sample to be analyzed is scanned with respect to a microscope objective. The luminescence is put through a single monochromator or a grating or prism to spectrally resolve the colors. The detector is a diode array that then records the colors that are emitted at a particular spatial position. The software then recreates the scanned image.

Decoding Multiple Fluorescence Emissions

When imaging samples labeled with multiple fluorophores, it is desirable to resolve spectrally the fluorescence from each discrete region within the sample. Such samples can arise, for example, from multiple types of SCNCs (and/or other fluorophores) being used to encode beads, from a single type of SCNC being used to encode beads but bound to a molecule labeled with a different fluorophore, or from multiple molecules labeled with different types of fluorophores bound at a single location.

Many techniques have been developed to solve this problem, including Fourier transform spectral imaging (Malik et al. (1996) J. Microsc. 182:133; Brenan et al. (1994) Appl. Opt. 33:7520) and Hadamard transform spectral imaging (Treado et al. (1989) Anal. Chem. 61:732A; Treado et al. (1990) Appl. Spectrosc. 44:1–4; Treado et al. (1990) Appl. Spectrosc. 44:1270; Hammaker et al. (1995) J. Mol. Struct. 348:135; Mei et al. (1996) J. Anal. Chem. 354:250; Flateley et al. (1993) Appl. Spectrosc. 47:1464), imaging through variable interference (Youvan (1994) Nature 369:79; Goldman et al. (1992) Biotechnology 10:1557), acousto-optical (Mortensen et al. (1996) IEEE Trans. Inst. Meas. 45:394; Turner et al. (1996) Appl. Spectrosc. 50:277) or liquid crystal filters (Morris et al. (1994) Appl. Spectrosc. 48:857) or simply scanning a slit or point across the sample surface (Colarusso et al. (1998) Appl. Spectrosc. 52:106A), all of which are capable of generating spectral and spatial information across a two-dimensional region of a sample.

One-dimensional spectral imaging can easily be achieved by projecting a fluorescent image onto the entrance slit of a linear spectrometer. In this configuration, spatial information is retained along the y-axis, while spectral information is dispersed along the x-axis (Empedocles et al. (1996) Phys.

Rev. Lett. 77(18):3873). The entrance slit restricts the spatial position of the light entering the spectrometer, defining the calibration for each spectrum. The width of the entrance slit, in part, defines the spectral resolution of the system.

Two-dimensional images can be obtained by eliminating the entrance slit and allowing the discrete images from individual points to define the spatial position of the light entering the spectrometer. In this case, the spectral resolution of the system is defined, in part, by the size of the discrete images. Since the spatial position of the light from each point varies across the x-axis, however, the calibration for each spectrum will be different, resulting in an error in the absolute energy values. Splitting the original image and passing one half through a dispersive grating to create a separate image and spectra can eliminate this calibration error. With appropriate alignment, a correlation can be made between the spatial position and the absolute spectral energy.

To avoid ambiguity between images that fall along the same horizontal line, a second beam-splitter can be added, with a second dispersive element oriented at 90 degrees to the original. By dispersing the image along two orthogonal directions, it is possible to unambiguously distinguish the spectra from each discrete point within the image. The spectral dispersion can be performed using gratings, for example holographic transmission gratings or standard reflection gratings. For example, using holographic transmission gratings, the original image is split into 2 (or 3) images at ratios that provide more light to the spectrally dispersed images, which have several sources of light loss, than the direct image. This method can be used to spectrally image a sample containing discrete point signals, for example in high throughput screening of discrete spectral images such as single molecules or ensembles of molecules immobilized on a substrate, and for highly parallel reading of spectrally encoded beads. The images are then projected onto a detector and the signals are recombined to produce an image that contains information about the amount of light within each band-pass.

Alternatively, techniques for calibrating point spectra within a two-dimensional image are unnecessary if an internal wavelength reference (the "reference channel") is included within the spectrally encoded material. The reference channel is preferably either the longest or shortest wavelength emitting fluorophore in the code. The known emission wavelength of the reference channel allows determination of the emission wavelengths of the fluorophores in the dispersed spectral code image. In addition to wavelength calibration, the reference channel can serve as an intensity calibration where coding schemes with multiple intensities at single emission wavelengths are used. Additionally, a fixed intensity of the reference channel can also be used as an internal calibration standard for the quantity of label bound to the surface of each bead.

In one system for reading spectrally encoded beads or materials, a confocal excitation source is scanned across the surface of a sample. When the source passes over an encoded bead, the fluorescence spectrum is acquired. By raster-scanning the point-excitation source over the sample, all of the beads within a sample can be read sequentially.

Optical tweezers can optionally be used to "sweep" spectrally encoded beads or any other type of bead into an ordered array as the beads are read. The "tweezers" can either be an infrared laser that does not excite any fluorophores within the beads, or a red laser that simultaneously traps the beads and also excites the fluorophores.

Optical tweezers can be focused to a tight spot in order to hold a micron-size bead at the center of this spot by "light pressure." Any bead smaller than approximately 10 µm in diameter that comes in contact with the focused spot will be pulled into the point of highest intensity. For beads that are larger than about 0.5 µm, only one bead can exist within the "trap" at a time. See, e.g., Ashkin (1997) *Proc. Natl. Acad. Sci USA* 94:4853–4860; Helmerson et al. (1997) *Clin. Chem.* 43:379–383; Quake et al. (1977) *Nature (London)* 388: 151–154; Ashkin (1972) *Sci. Amer.* 226:63–71; Ashkin (1970) *Phys. Rev. Lett.* 24:156–159.

Optical tweezers can be used to hold spectrally encoded beads and to order them for reading. The tweezers can be focused near the bottom of a well located at the center of the detection region of a point-scanning reader, which can use the same optical path. The reader and tweezers can be scanned together so that they are always in the same position relative to each other.

For example, if the tweezers are turned on at spot-1, any bead contacted by the tweezers will be pulled into the center of the trap, ensuring an accurate quantitative measure of the assay label intensity. After reading the first bead, the tweezers are turned off to release it, and the scanner advances to the right just far enough to prevent the first bead from being retrapped before the tweezers are turned on again and then moved immediately to spot-2. In the process, any bead contacted by the tweezers would be trapped and brought to spot-2, where it is read. Choosing a scan distance that corresponds to the average interbead spacing can minimize bead loss from multiple beads occurring between sampling points.

Alternatively, the optical tweezers can be focused within the solution away from the surface of the well. As the tweezers are turned on and off, the solution is mixed, so that different beads are brought into the detection region and held while they are scanned.

In another alternative, the optical tweezers can be focused in only one dimension, i.e., to a line rather than a spot, thus creating a linear trap region. This type of system can be used to sweep beads into distinct lines that can be scanned by a "line scanning" bead reader.

The Molecular Beacon on a Bead

Figure 1B:
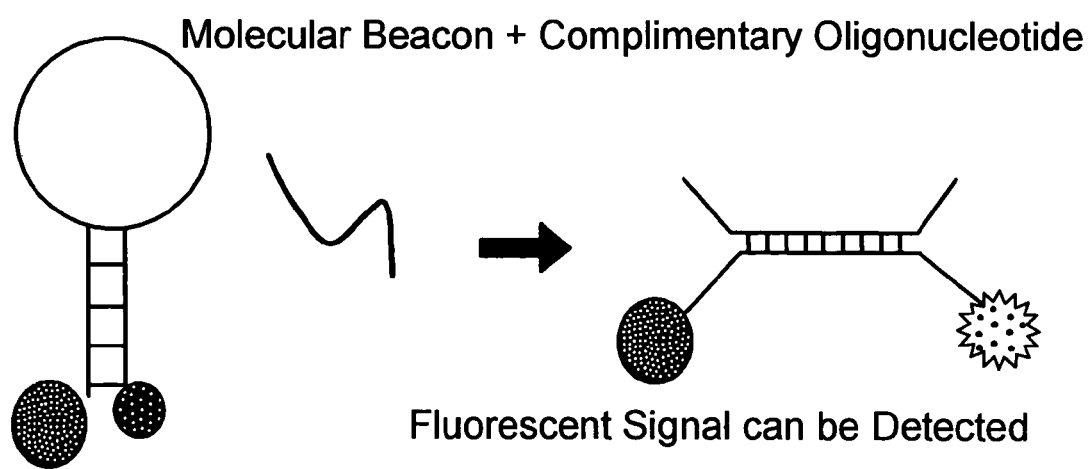
FIG. 1B depicts the molecular beacon shown in FIG. 1A hybridized to a complementary oligonucleotide such that the molecular beacon does not form the stem-loop structure and the quencher thus does not quench the fluorescence emission from the fluorophore.

Tyagi et al. (1996) *Nature Biotech.* 303–308 describe an oligonucleotide probe that is optically silent in solution but fluoresces upon hybridization with a complementary target. The probe is a single-stranded oligonucleotide that possesses a stem-and-loop structure. The loop is a sequence at least part of which complementary to at least part of the target. One arm of the stem has a fluorescent moiety attached and the other arm has a nonfluorescent quenching moiety attached. The two arms are complementary to one another. In the nonhybridized state, the stem keeps the two moieties in sufficiently close proximity so that the nonfluorescent moiety quenches the fluorescent moiety. Upon hybridization, the consonant conformational change in the probe forces the arm sequences apart and allows detection of the fluorescent moiety. Molecular beacons (MBS) are oligonucleotide probes used for detection of specific nucleic acids in homogeneous solution. These oligonucleotides are hairpin shaped where the loop portion (typically 15–30 nucleotides in length) is a probe sequence complementary to the target nucleic acid molecule. The stem portion (typically 4–7 nucleotides) is formed by annealing the complementary arm sequences (3' and 5') of the polynucleotide. A fluorophore can be attached to one end of the MB and a quencher such as DABCYL is attached to the other end (see FIG. 1a). In the absence of target nucleic acid, the stem keeps the two moieties in close proximity to each other, causing the fluorescence to be quenched by energy transfer. When the complementary target to the loop is present, the loop sequence will form a hybrid with the target nucleic acid that is longer and more stable than the stem. The MB is thus linearized, causing the fluorophore and the quencher to be far away from each other, leading to the restoration of fluorescence (see FIG. 1b). The number of non-overlapping dyes available has thus far limited the use of MBs in homogeneous solution.

The invention described here is attachment of MBs onto encoded microspheres dyed with one or more different kind of SCNCs. This method can be used to detect specific nucleic acid (RNA or DNA) sequences, e.g. mRNA, cDNA, strains of different bacterium, single nucleotide polymorphism (SNP), mutations etc.

Figure 4:
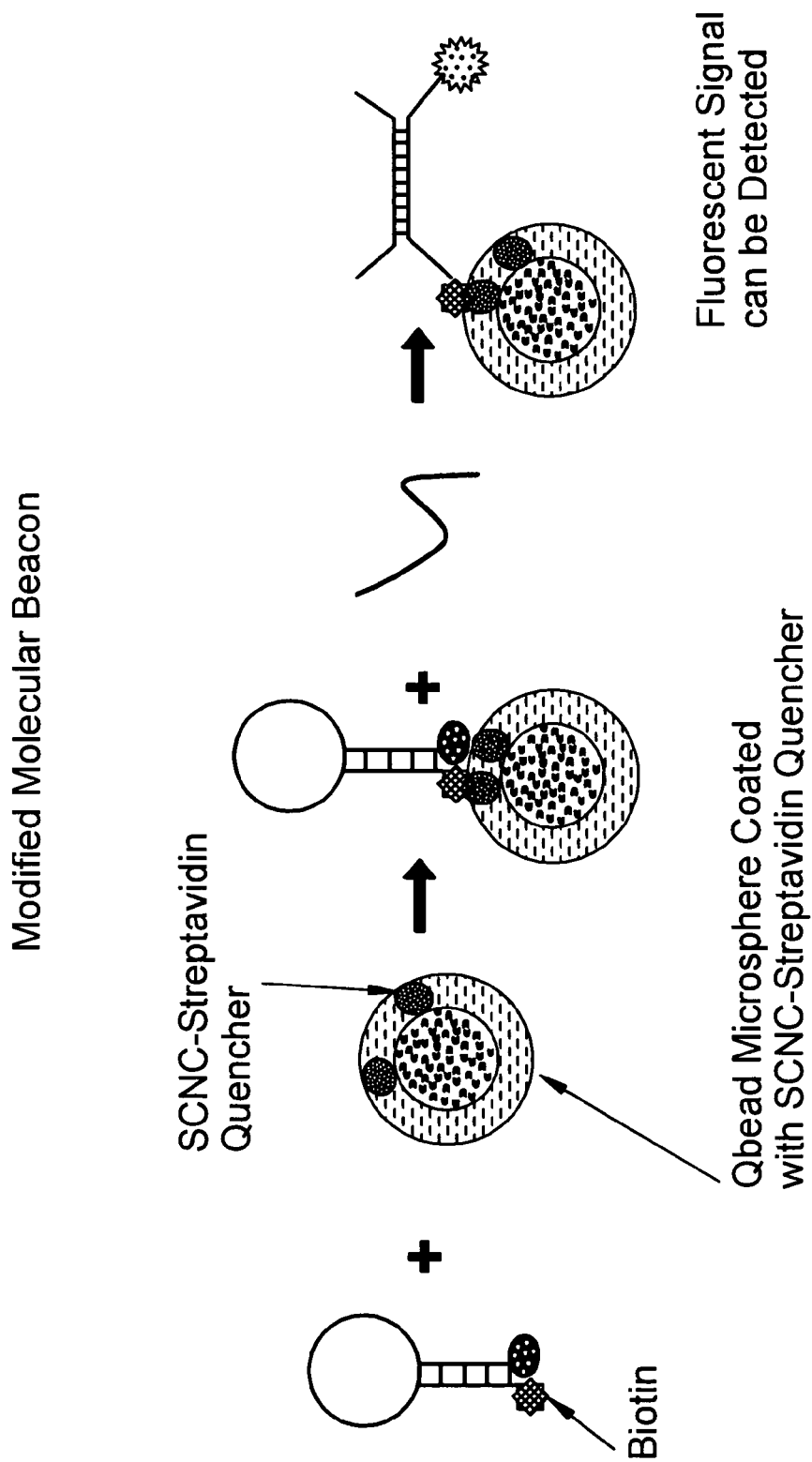
FIG. 4 shows another variation in which the quencher is located on the surface of the encoded microsphere along with streptavidin, and the molecular beacon is linked to a biotin molecule at one end and a reporter fluorophore at the other end. The biotin molecule binds to the streptavidin and localizes the molecular beacon to the surface of the bead, where the quencher can quench the fluorescence emission from the reporter in the absence of target polynucleotide. When hybridized to the target polynucleotide, however, the reporter moves away from the quencher and its fluorescence emission increases.

This method can advantageously be multiplexed with the number of MBs that can be used in one well only limited by the number of different encoded microspheres (See FIG. 4). This method can be quantitative. Compared to conventional dyes SCNCs are highly photostable, have higher quantum yield and narrower emission spectra. A smaller amount of sample is required for each assay as this assay can be multiplexed and the signals concentrated on the beads. When SCNCs are used for both the reporter and quencher, multiple different SCNCs can be used as reporter on the same bead, thus providing two or more results on the same bead.

A MB consists of two approximately 4–7 base pair complementary sequences so that under normal conditions it forms a hairpin stem loop. The loop of each MB comprises 15 or more nucleotides in length. A quencher dye or SCNC is attached at or nearer one end of the oligonucleotide and another dye or SCNC reporter at the other end of the MB. Each of these attachments can be direct or indirect. One of the quencher and reporter can be found on the bead. The position of the quencher SCNC and the reporter SCNC can be interchanged (see FIGS. 4–6). A "spacer," (e.g., a string of nucleotides or carbon chains) is linked preferably to the quencher species. The target polynucleotides for this assay are, preferably, unlabelled RNA, cDNA, or DNA. In the presence of complementary target in the specimen or sample, the hairpin oligonucleotide is linearized as the loop part of the oligonucleotide hybridizes to the target. The quencher species then moves away from the reporter species allowing a fluorescent signal to be detected quantitatively.

Different MBs can be conjugated onto SCNC-encoded microspheres (any size) of different colors or color combinations for multiplexing. The signature of the encoded microspheres is detected to identity the nature of the MB on the microsphere. The stem of the MB can be designed so that the interaction between the two members thereof is strong enough to form the hairpin structure for efficient fluorescence quenching, yet weak enough to dissociate when a polynucleotide complementary to the loop is present in the specimen or sample.

Alternatively, different microspheres can embedded with a layer of an SCNC quencher, e.g., a SCNC with a broad emission spectrum and low quantum yield in the spectral region of interest, on the outer surface of the microsphere or on the outside of the bead. Each oligonucleotide will have complementary sequences at both ends so that under normal conditions it will form a hairpin loop (see FIG. 4).

Figure 3:
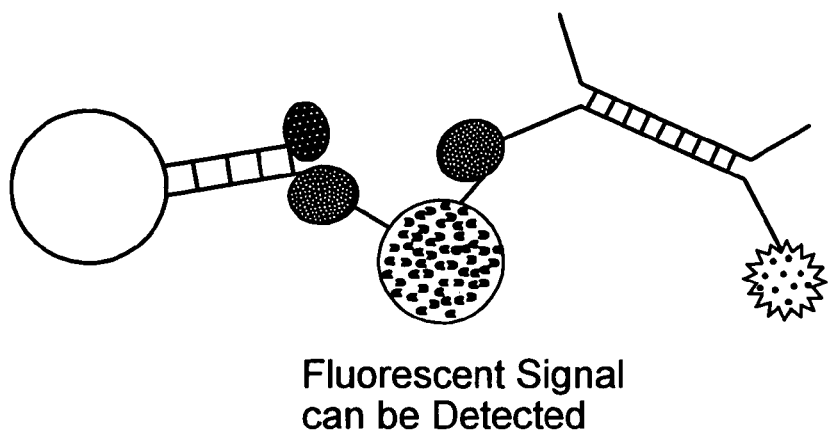
FIG. 3 shows a variation of the molecular beacon shown in FIG. 2, in which the quencher is attached to the distal end of the molecular beacon, and the reporter fluorophore bridges the molecular beacon and the microsphere. Binding of the molecular beacon to its target polynucleotide moves the quencher away from the reporter, thereby increasing its fluorescence emission upon excitation.

Different color SCNC reporters can be attached at the end of different MB (if more than one assay is being tested) on the same bead. This may be useful for detecting different mutations in a nucleic acid sequence (see FIG. 3).

Figure 2:
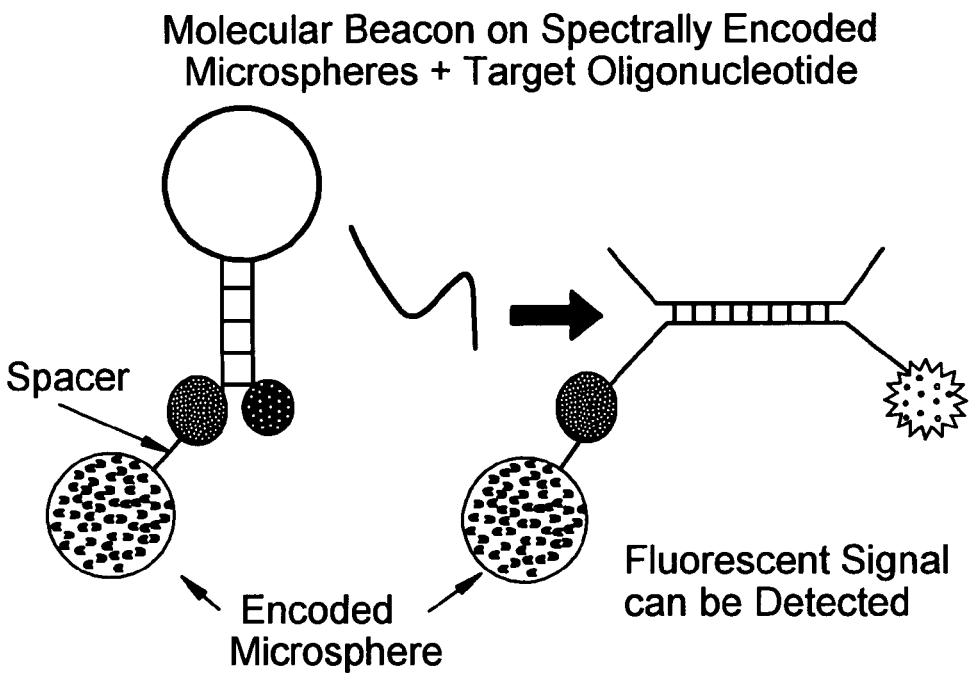
FIG. 2 shows a molecular beacon coupled through a spacer to a microsphere encoded with a spectral code comprising semiconductor nanocrystal(s), wherein the molecular beacon forms the stem-loop structure and the fluorophore is quenched in the absence of hybridization to the target oligonucleotide, and wherein hybridization to the target oligonucleotide allows fluorescence from the fluorophore to be detected when the molecular beacon is hybridized to the target polynucleotide. Note that the fluorophore can also be self-quenching and located in the molecular beacon such that its fluorescence emission is quenched either when the stem-loop structure is formed or when the molecular beacon is hybridized to the target polynucleotide, but not under both states.
Figure 5:
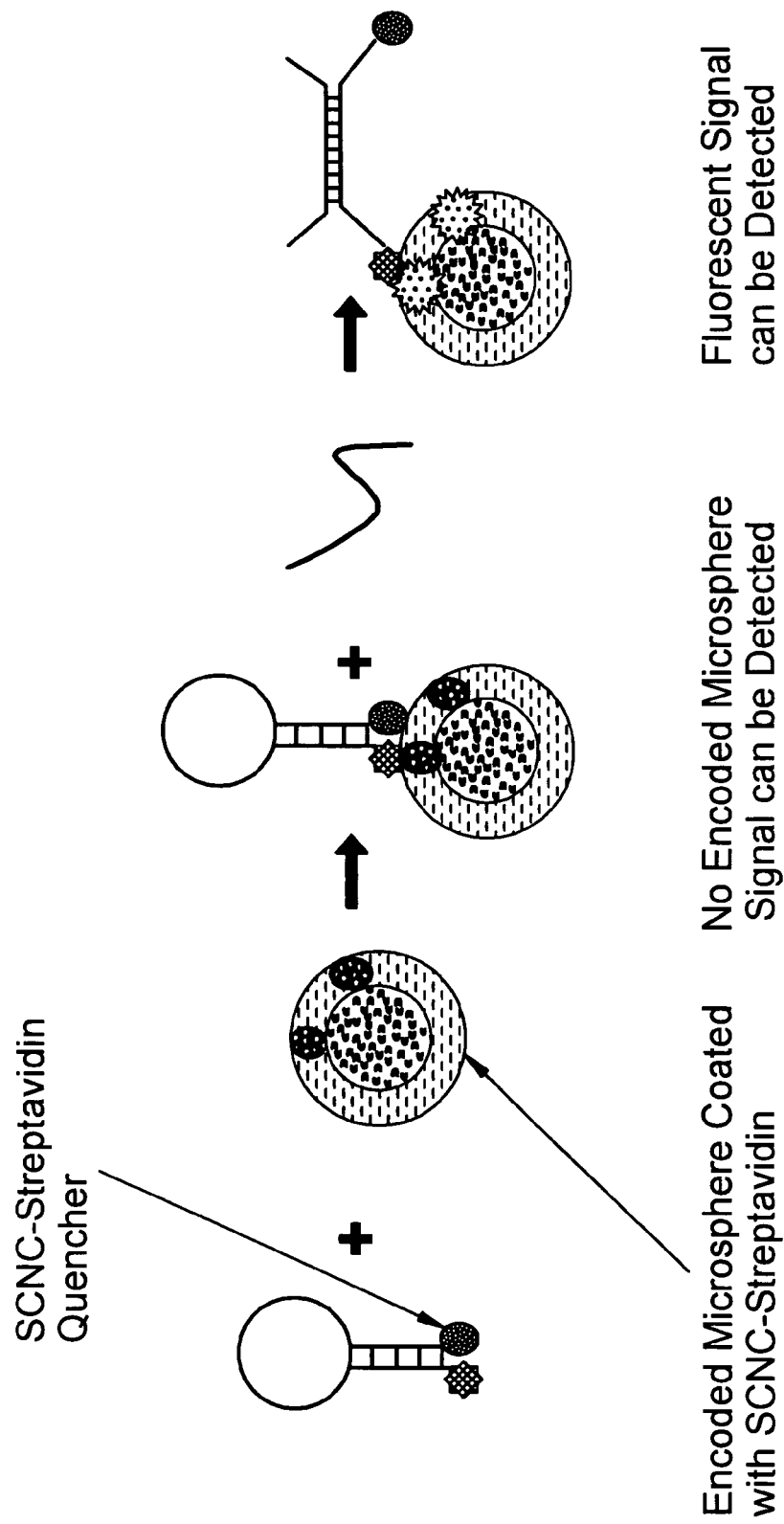
FIG. 5 shows the converse variation to that shown in FIG. 4, in which the quencher is located at the distal end of the molecular beacon, and the reporter fluorophore is located on the surface of the microsphere along with streptavidin. The molecular beacon is again linked to the microsphere via a biotin molecule. Hybridization of the molecular beacon to the target polynucleotide moves the quencher away from the surface of the microsphere and allows the fluorophores on the surface of the bead to have increased fluorescence emission.
Figure 6:
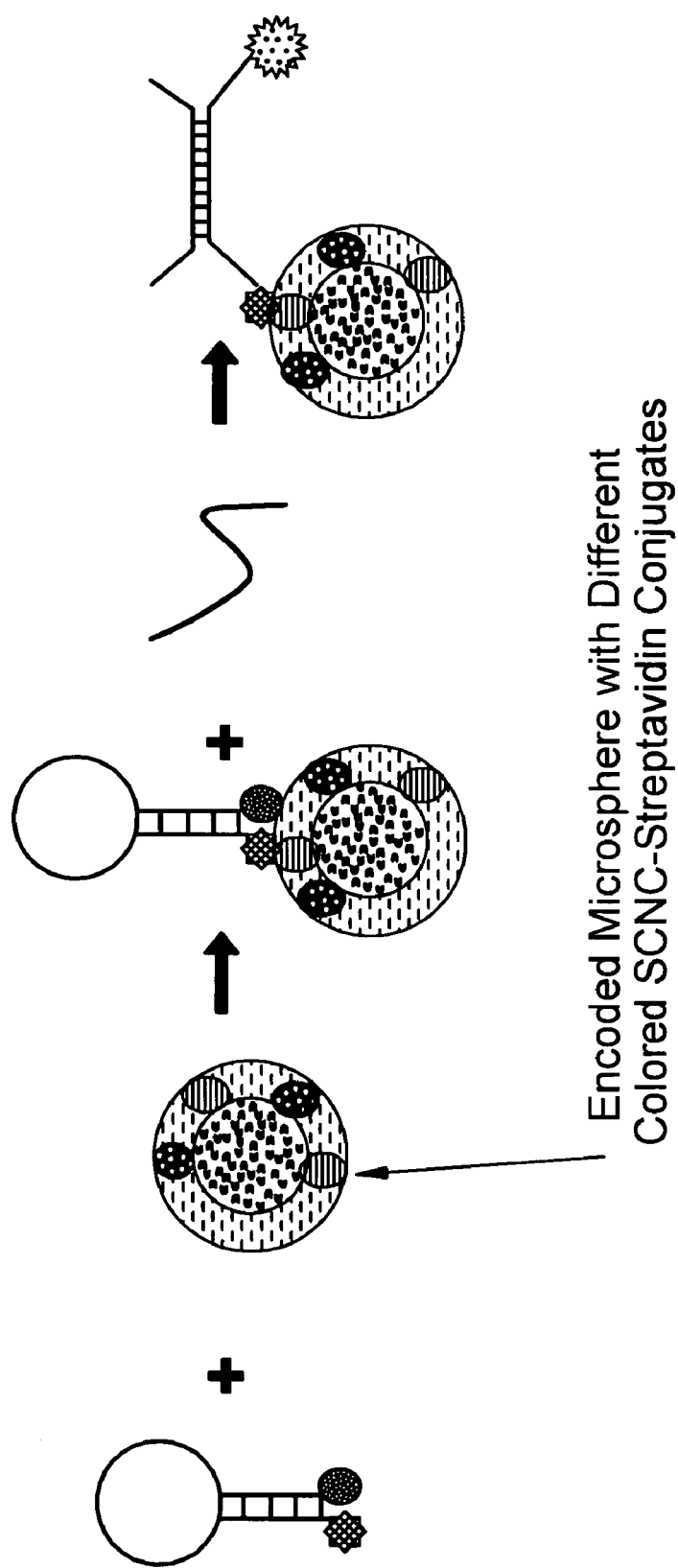
FIG. 6 shows a variation similar to that shown in FIG. 5; however, the surface of the microsphere is coated with different colored SCNCs such that upon hybridization of the molecular beacon to the target polynucleotide, a plurality of fluorescence emissions increases from the surface of the microsphere.

A quencher SCNC-1 is attached at one end of the oligonucleotide and SCNC-2 reporter at the junction between the spacer and the MB (see FIGS. 2 and 5). The position of the quencher SCNC-1 and the reporter SCNC-2 can be interchanged. For example, the SCNC-2 reporter can be at the end of the oligonucleotide (3' or 5') and the quencher SCNC-1 can be located at the junction between the spacer and the MB. Alternatively, Biotinylated MBs can bind covalently to streptavidin-coated encoded microspheres. In this case, the addition biotin can be placed in the stem of the MB or at the end of the spacer.

Encoded microspheres can also coated with a layer of SCNC-1 quencher-streptavidin conjugate on the outside of the bead. This can be done, for example, by using biotinylated encoded microspheres. The modified MB comprises complementary sequences at both ends of the oligonucleotide for hairpin loop formation with biotin attached to one end and the SCNC-2 or a dye reporter attached to the other end of the oligonucleotide away from the bead. In the absence of target nucleic acid, the reporter SCNC-2 or dye signal will be quenched by the SCNC-1 quencher on the surface of the bead. In the presence of complementary target in the specimen or sample, the hairpin oligonucleotide is linearized as the loop part of the oligonucleotide hybridizes to the target. The quencher species then moves away from the SCNC reporter species allowing fluorescent signal to be detected quantitatively (see FIG. 4).

The Cleavase Assay

Cleavase is a flap endonuclease that recognizes 'flap' structures and cleaves the non-complementary overhanging part of the nucleic acid. Cleavase enzymes optimized for DNA or RNA substrates are available. The cleaved probe can be assayed using FRET, or by extension of the now-cleaved primer (see, e.g., Lyamichev et al. (1999) *Nature Biotechnol.* 17:292–296; Griffin et al. (1999) *Proc. Natl. Acad. Sci. USA* 96:6301–6306). In previous embodiments, the cleavase assay cannot be multiplexed. This invention allows cleavase assays to be carried out in a multiplexed fashion, and, with an optional signal amplification step, allows very sensitive measurements to be made.

Oligonucleotides are attached to spectrally encoded microspheres, as described above, with the 5' end of the oligonucleotide tethered to the microsphere, a 3' assay-specific oligonucleotide and, flanked thereby, a linker. A different assay-specific oligonucleotide is attached to a particular and distinct spectrally encoded bead. The assay is read using one of several different devices to decode the spectral code and generate assay signal, but preferably one which allows sensitive detection of assay signal.

Figure 7A:
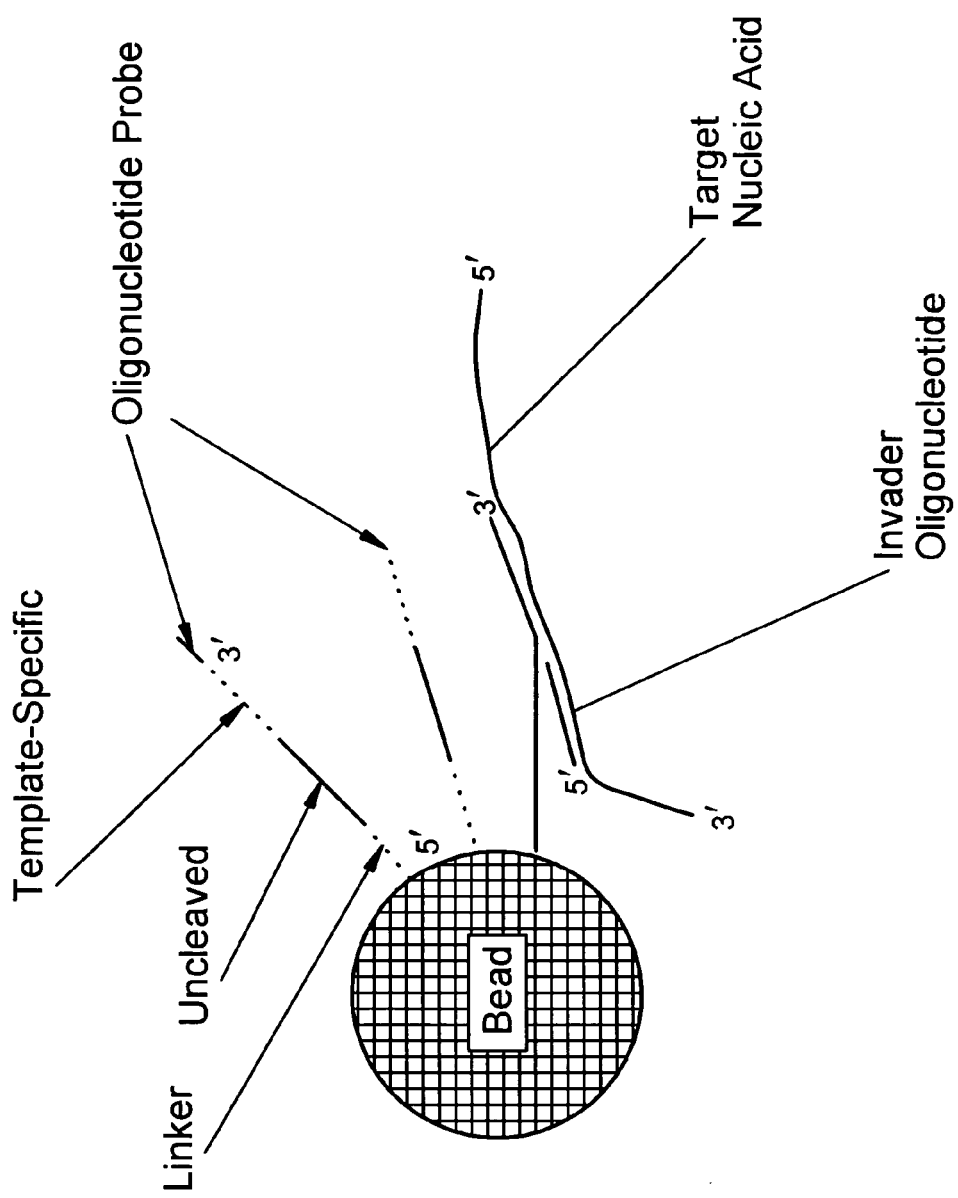
FIG. 7A shows a cleavase assay being performed on the surface of an encoded bead. The oligonucleotide probe linked to the bead can be labeled or unlabeled prior to cleavage. A target nucleic acid is shown as hybridized to one oligonucleotide probe linked to the bead. An invader oligonucleotide is also shown simultaneously hybridized to the target nucleic acid.
Figure 7B:
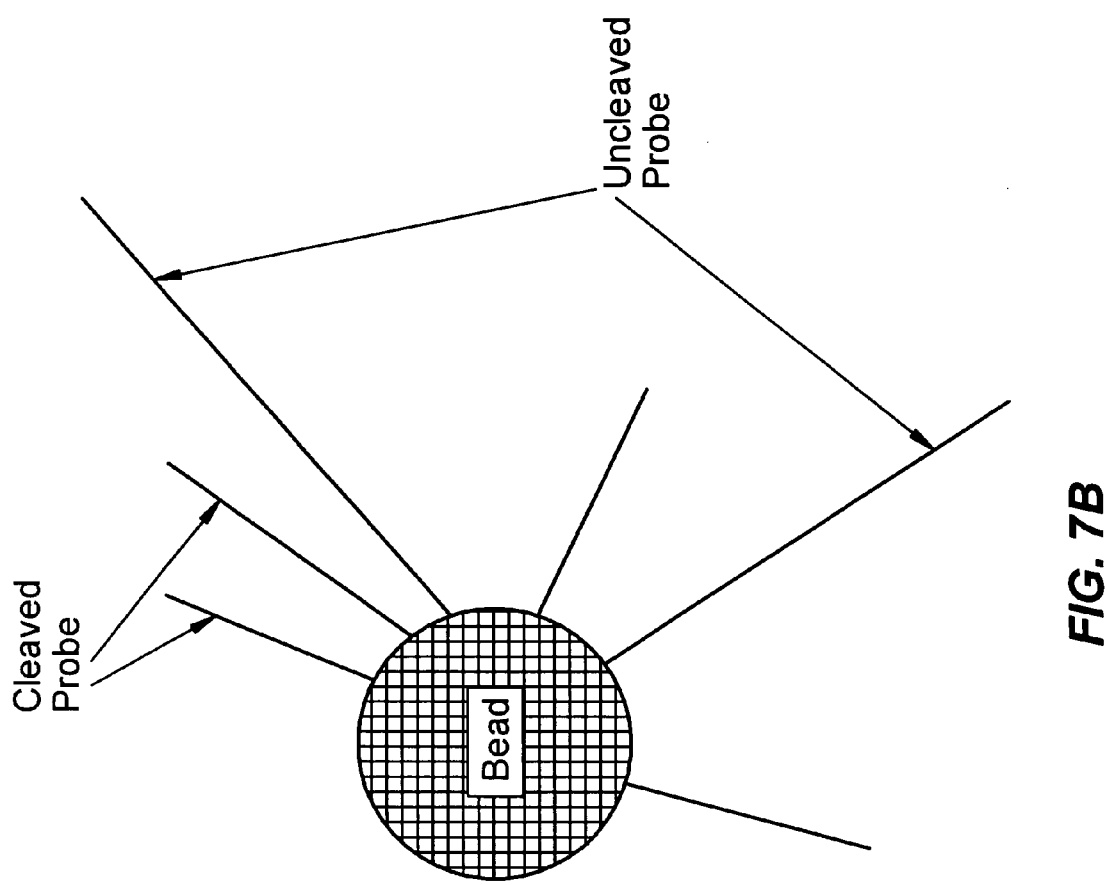
FIG. 7B shows a bead after performing a cleavase assay; some of the oligonucleotide probes linked to the bead are shown as cleaved, and some are uncleaved. The amount of cleavage is proportional to the amount of target nucleic acid present in the sample.

FIG. 7 shows a schematic of how a single assay proceeds. A bead is coated with oligonucleotides of the same sequence. The 5' end of the oligonucleotide is tethered to the bead. The 3' portion of the oligonucleotide (around 5–20 bases) is complementary to part of the target oligonucleotide. Another "invader" oligonucleotide is also designed to be complementary to the target oligonucleotide and is free in solution. This invader oligonucleotide is designed to have its 3' end overlapping one base with the 5' oligonucleotide-specific part of the bead-tethered oligonucleotide. When these two oligonucleotides hybridize to the template in the presence of the cleavase enzyme, in appropriate buffer and temperature conditions, the enzyme cleaves the bead-tethered oligonucleotide. The cleaved part of the oligonucleotide that is still bound to the template has a lower Tm than the invader oligonucleotide so that it will denature from the template at a higher rate than the invader oligonucleotide.

The invader oligonucleotide, and template are then free to dissociate from the bead and to become bound to an unreacted bead-tethered oligonucleotide, repeating the process in an isothermal fashion. Measurement of the amount of cleavage for each individual bead gives a measure of the amount of template present.

Multiplexed assays (quantitation of more than one template oligonucleotide simultaneously) can be carried out by attaching different template-specific oligonucleotides to different spectrally encoded beads. A different invader oligonucleotide must be synthesized for each different template sequence when multiplexed. The cleavage for each different spectrally encoded bead is dependent on the amount of template present that is complementary to the oligonucleotide that is attached to the bead. Quantitation of the cleavage from each spectrally encoded bead gives a measure of the amount of complementary template present.

This cleavage is known to be dependent on perfectly paired bases in the region of the flap structure. If there are one or more bases difference between the template and the bead-tethered oligonucleotide at, or near to, the position where it abuts the invader oligonucleotide then the cleavase will cleave at a much reduced rate, if at all. Mismatches between the template and close to the 3' end of the invader oligonucleotide have the same effect. This allows the assay to be used to genotype single nucleotide polymorphisms.

Figure 8A:
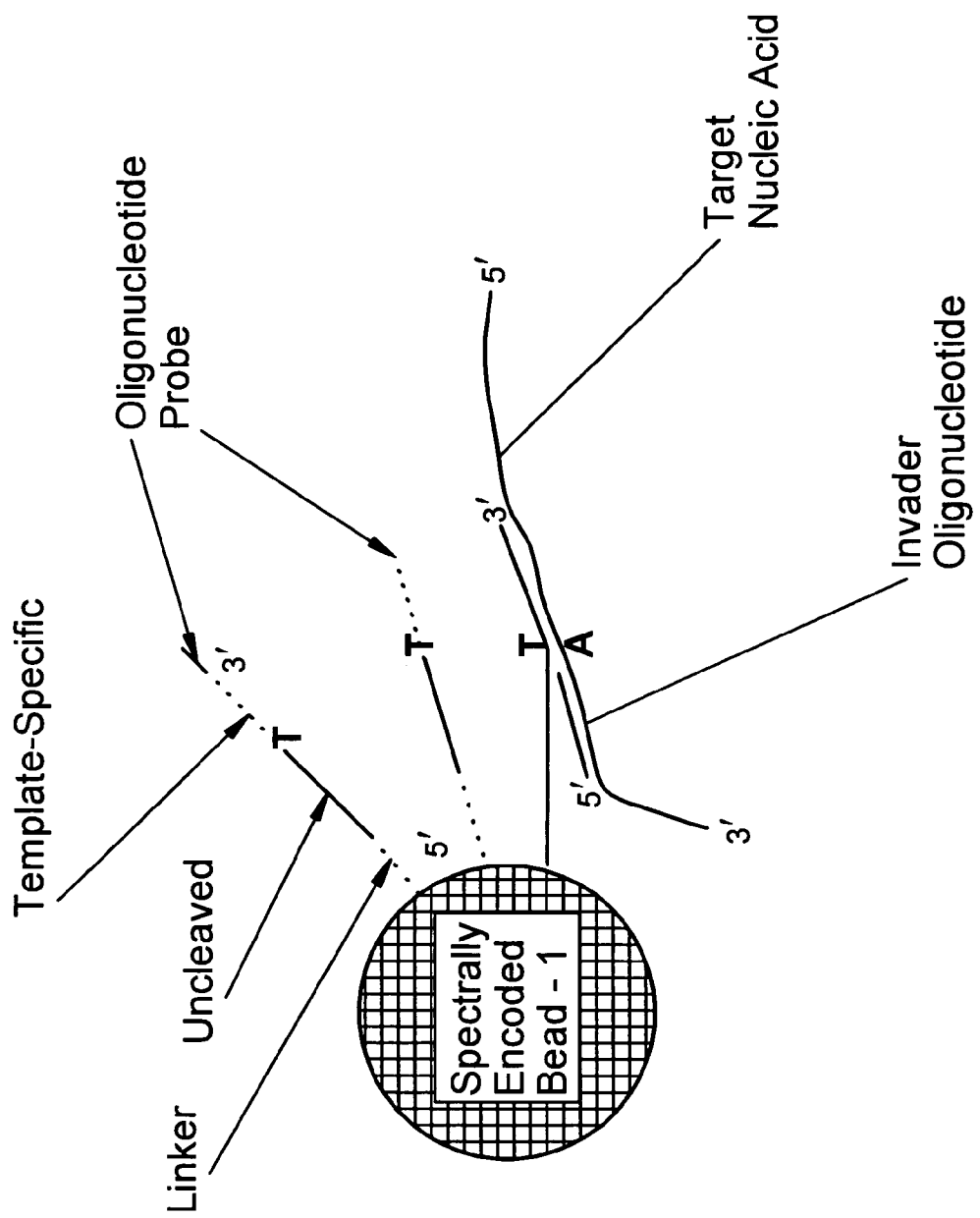
FIGS. 8A and 8B show two different spectrally encoded beads respectively conjugated to two different oligonucleotide probes complementary to two different variants of a target nucleotide sequence which differ by a single base. The base difference is located in sufficient proximity to the nucleotide which is displaced by the invader oligonucleotide such that the cleavase enzyme will not cleave the oligonucleotide probe when hybridized to the incorrect target nucleic acid: the oligonucleotide on bead 1 is cleaved only if the T is present, while the oligonucleotide on bead 2 is cleaved only if the A is present. More than one allele may possess the same single nucleotide polymorphism, such that either single assay detects a plurality of alleles.
Figure 8B:
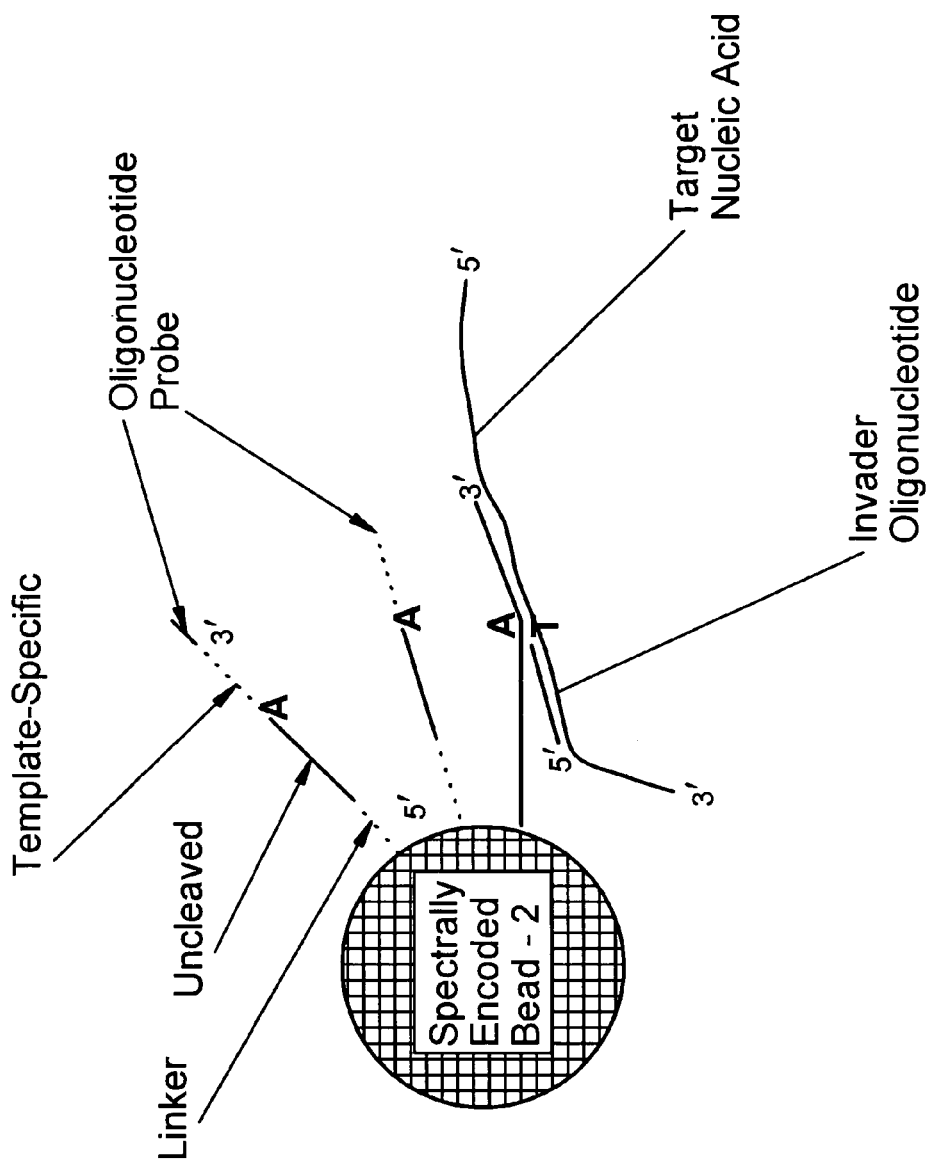

In the case of these bead-based assays, allele specific cleavage can be carried out for more than one allele simultaneously. This is done by designing the bead-tethered oligonucleotide to be allele specific (see FIG. 8), so that an oligonucleotide specific for one allele is attached to one spectrally encoded bead and an oligonucleotide specific for another allele is attached to a different spectrally encoded bead. Allele-specific means perfectly complementary to one allele but not the others. The bead-tethered oligonucleotide is designed so that the polymorphic base(s) is at or close to the 5' end of the template specific part of the oligonucleotide. This generates allele specific cleavage in an invader reaction. When multiple spectrally encoded beads, each attached to a different allele-specific sequence, are mixed together in the assay, quantitation of the relative amounts of cleavage can be used to indicate presence/absence of alleles and to generate genotype data. Alternatively, the polymorphic sequence can be paired with the invader oligonucleotide at, or close to, its 3' end. In this case, the same encoded bead can be used, but separate reactions would be carried out for each allele.

As shown in FIG. 9, if a detectable label has been incorporated in, or at the end of, the template-specific part of the bead-tethered oligonucleotide, this moiety will become detached from the bead following-cleavage (and subsequent optional washing). Suitable detectable moieties include organic fluorophores (that do not overlap spectrally with the spectral code), SCNC™ semiconductor nanocrystals (SCNC), and haptens like biotin (that can be bound to streptavidin-fluorophore, streptavidin-SCNC™ SCNC, or other signal generating compounds). Measurement of the reduction in this signal (compared to the negative control) gives an indication of the amount of cleavage that has occurred.

Fluorescence resonant energy transfer (FRET) can be used if a reporter (fluorescent dye, SCNC™ SCNC, etc.) and quencher are initially attached at either side of the cleavage site. Once cleavage has occurred, the quencher is removed from the proximity of the reporter and the reporter remains bound to the bead. Therefore, increased cleavage leads to increased luminescence, which is detected by measuring the luminescence at an appropriate wavelength for the fluorescent reporter.

Figure 10:
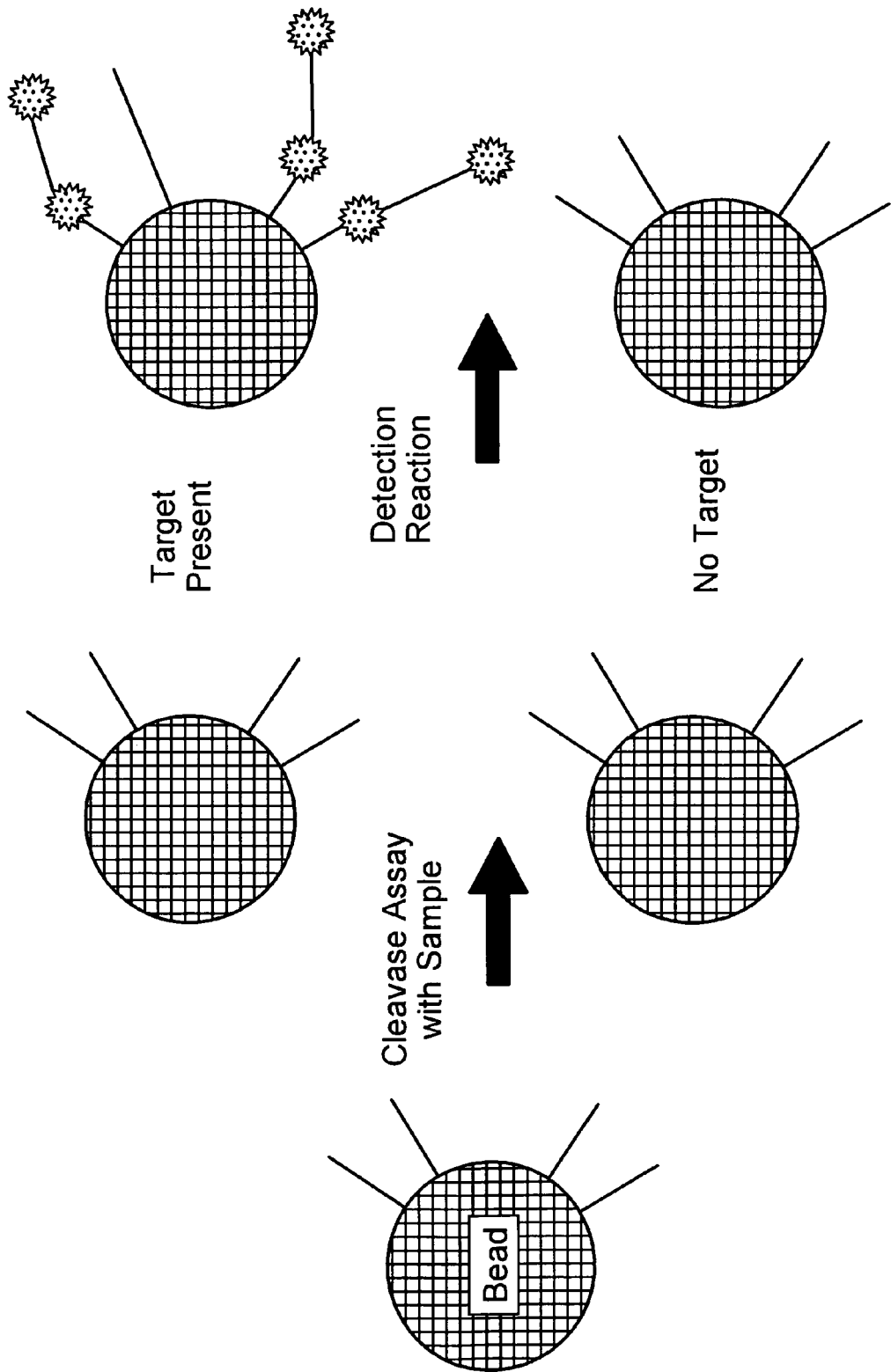
FIG. 10 shows another variation of the cleavase on a bead assay in which the oligonucleotide is initially unlabeled and lacks a free distal end for attachment of a label; cleavage of the oligonucleotide in the presence of target nucleic acid unveils a free distal end which can be linked to a label through a variety of methods.

FIG. 10 shows the concept of this method. Here, the part of the cleaved probe that remains attached to the bead has a 3'-OH group and is therefore amenable to extension with dNTPs, or ligation with 5' phosphorylated oligonucleotides, that are labeled The cleaved probe can be detected using terminal deoxynucleotidyl transferase to incorporate many labeled nucleotides. The uncleaved bead-tethered oligonucleotide must be modified at its 3' end to prevent it from being able to extend. This can be done in a variety of ways including using CPG synthesis supports, such as a 3' C3 spacer, or a 3'-phosphorylation (Glenn Research) that leave a 3' end that cannot be extended, or using post-synthetic methods to phosphorylate the 3'-OH group, or by using terminal transferase to incorporate a ddNTP at the 3' end of the oligonucleotide prior to carrying out the assay. For the best sensitivity, a modification that (1) remains 100% (or close to 100%) complete and (2) provides 100% (or close to 100%) inhibition of extension is required. This modification to the probe is necessary when using the terminal transferase method and may be desirable when using other methods (below) that require hybridization to a template.

When using primer extension to detect cleavage, a second template (different from the sample being tested) is used that hybridizes to the cleaved probe and allows it to extend and incorporate labeled nucleotides, in the presence of appropriate polymerase, buffer, temperature, etc. The uncleaved oligonucleotide does not extend, as it is not complementary at its 3' end to this second template. Measurement of the incorporated signal therefore gives a measure of the amount of cleavage that has occurred. A thermal cycling reaction would allow more complete extension of the cleavage-produced primers. Washing of the beads between cleavage and extension may be required to reduce non-specific extension on the first template.

The second template that is used can be a circularized template, in order to initiate rolling circle replication and hence incorporate a large number of labeled nucleotides (see Lizardi et al. (1998) *Nature Genetics* 19:225–232).

Ligation can be used as the method to detect the cleaved oligonucleotide. A second template is used to coordinate the ligation of the cleaved probe to another oligonucleotide labeled with a detection moiety. This reaction is unlikely to be susceptible to non-specific ligation of the uncleaved probe as the second template and labeled oligonucleotide can be chosen to be very specific. The uncleaved bead-bound oligonucleotide may also be modified at its 3' end, as before, to prevent any activity in a ligation reaction.

A dual assay format called "invader squared" uses the 3' part of the cleaved probe as the invader probe in a different cleavase reaction on a different template. These reactions proceed simultaneously in the same reaction tube and provide geometric amplification. In the FRET-based detection format used in the solution-phase assay, this allows generic FRET probes to be used for many assays, as the cleavage of this FRET probe is carried out due to the hybridization of the FRET probe to an artificial (not part of the sample) template and the creation of the invader probe from the assay specific reaction. Generic beads (i.e., with oligonucleotides attached that have nucleic acid sequences that are specific to artificially introduced templates, not to the sample) can be produced to detect the specific cleavage of many different probes due to the creation of specific invader probes for these beads.

The Loop Probe Assay

Figure 11:
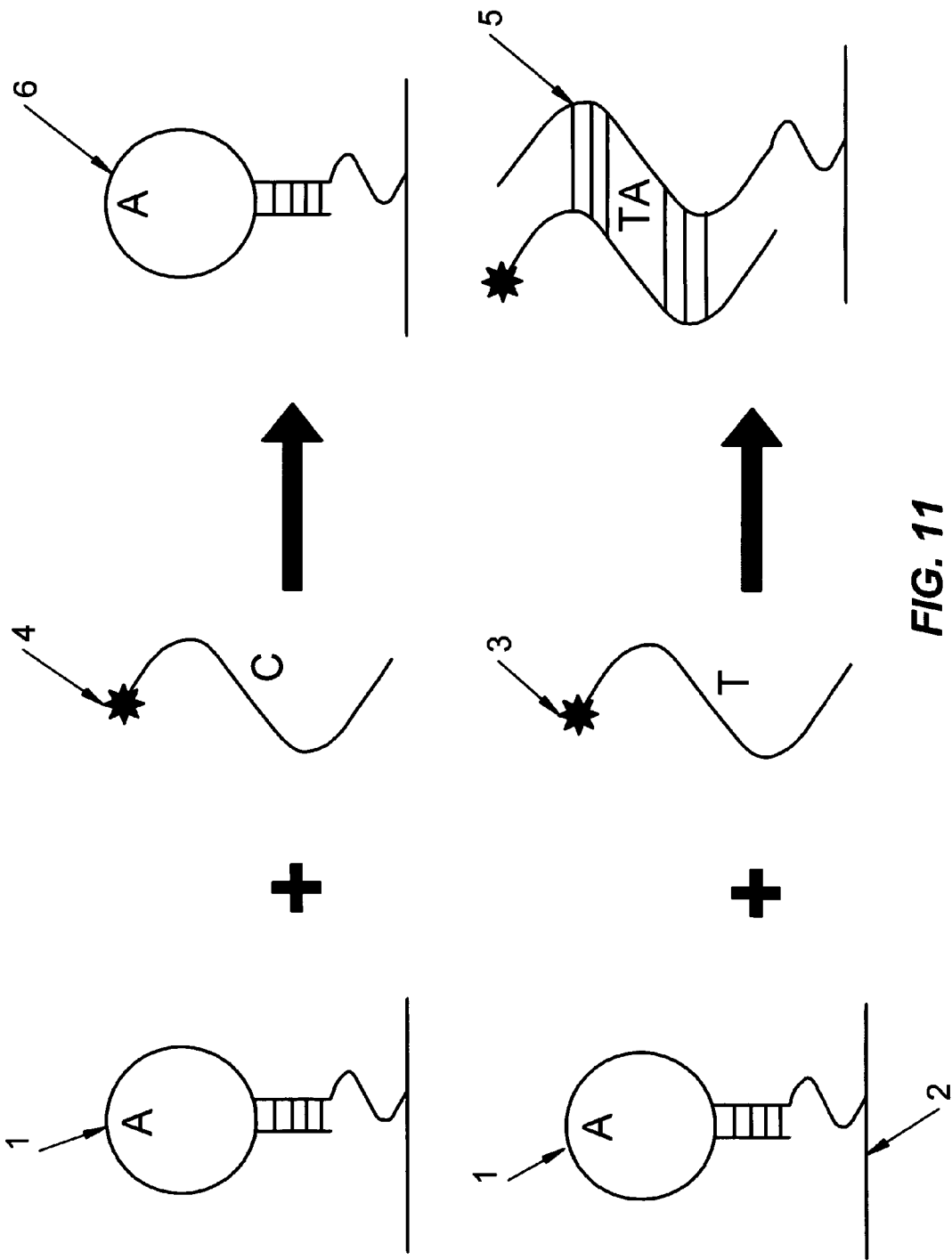
FIG. 11 is a depiction of a loop probe assay used to selectively detect a SNP allele.

In the loop probe hybridization assay illustrate in FIG. 11, an oligonucleotide hairpin structure similar to a molecular beacon is designed and synthesized. This oligonucleotide preferably contains a 4–7 base complementary sequence between the 3' and 5' ends of the oligonucleotide to form the stem-loop secondary structure. Between the stem sequences is placed the sequence which will be complementary to at least a part of the polynucleotide target. The 5' end of the oligonucleotide is labeled with a linker that is capable of conjugating to a solid support, such as an amino-linker. Neither a reporter nor a quencher dye is required.

This oligonucleotide is conjugated to a substrates, which need not be a microsphere, via any one of a number of standard coupling chemistries. Unbound oligonucleotide probe is washed away. This oligonucleotide probe folds and form the hairpin secondary structure predicted using an oligonucleotide-folding program.

A polymerase chain reaction (PCR) using a labeled primer can be performed to generate the labeled polynucleotide target, which is complementary to the capture probe on the surface of the bead. This PCR-amplified DNA target is denatured or made single-stranded by heat or base treatment. This solution containing single, base complementary targets is then placed into solution with the beads conjugated to capture probes. The target strand is complementary to and hybridizes with the capture probe sequence.

The secondary structure within the capture probe will only allow the completely complementary target to open up the secondary structure and specifically bind. A single nucleotide polymorphism is sufficient to disrupt the binding, and prevent the mismatched probe from being accessible for hybridization.

Factors for optimization of this assay include stem length and GC content, probe loop length and GC content, probe loop oligonucleotide spacer length, target concentration, target amplicon length, assay temperature, assay salt concentration, and assay incubation time.

In one preferred multiplexed embodiment, two primers are used to generate PCR amplified target. The primer which extends to form the strand to be captured is 5' end labeled with fluorescein during oligonucleotide synthesis. These two primers are selected to amplify the region flanking an SNP.

Two capture probe sequences are selected, one each complementary to the two alleles of the SNP. These probes are chosen using the same oligonucleotide folding programs used to design the sequence of molecular beacons. The stem length typically varies from 4–7 nucleotides. The 5' end of each oligonucleotide is chemically tailed with an amino-linker.

Two different spectrally encoded microspheres are created. These two sets of beads are spectrally distinct. The surface of the microspheres contains carboxyl groups. Each aminated oligonucleotide capture probe is conjugated to one of the spectrally encoded carboxyl beads via a standard EDC coupling reaction. Unbound oligonucleotide is washed away. A PCR reaction using a fluorescein labeled primer is performed to generate the several DNA targets, which contain an SNP within their sequence. This PCR amplified DNA target is denatured or made single-stranded by heat or base treatment. The solution containing the complementary target is then placed into the solution with the capture probes conjugated beads. The target strand that is complementary to the capture probe sequence opens up the loop and binds. The target that is not complementary to the capture probe sequence will not open the loop, and will not bind. This specificity can be achieved across a wide range of temperature optima typically from approximately 30–45° C.

Alternatively, the PCR primer is biotinylated instead of fluoresceinated. After the capture reaction is performed, the unbound target is washed away, and a detection reaction is performed via a fluorophore conjugated to streptavidin. This fluorophore could be a semiconductor nanocrystal as the reporter.

Use of the Methods with Microarrays

Microarray slides attached to polynucleotides can be prepared as described at www.nhgri.nih.gov/DIR/Microarray/fabrication.html, also set forth in U.S. patent application Ser. No. 09/675,528 by Empedocles et al. entitled "Microarray Methods Utilizing Semiconductor Nanocrystals", filed Sep. 29, 2000. Further guidance on fabrication, sample labeling and conditions for hybridization using microarrays is provided, for example, by Bittner M., et al. (2000) Nature 406:536–540; Khan J., et al. (1999) Electrophoresis 20:223–9; Duggan, D. J. (1999) Science 283:83–87; and DeRisi, J. et al. (1996) Nature Genet. 14:457–60.

In a typical microarray experiment, the sample suspected of containing the target polynucleotide is treated to form a labeled amplification product. The amplification products are optionally mixed with blockers, for example tRNA, Cot1 DNA, or purified repeat sequences such as LINE or Alu sequences, or mixtures thereof. Nonnucleotide blocking agents can also be used, including proteins, for example BSA, and detergents. This mixture is then incubated with the microarray slides. The excess probes are removed and the slides scanned.

The microarray can then be scanned with a laser scanner having an excitation source and emission filters appropriate for the particular SCNC(s) or other fluorophore used, or the microarray can be scanned with a wide-field imaging scanner having appropriate excitation and emission filters.

Kits

Kits comprising reagents useful for performing the methods of the invention are also provided. In one embodiment, a kit comprises a substrate attached to a polynucleotide. The substrate can be an encoded bead conjugate comprising a first spectral code comprising a first semiconductor nanocrystal and first fluorescence characteristics.

The polynucleotide can have a sequence suitable for performing a cleavase assay for the target polynucleotide, or may form a stem-loop structure. The polynucleotide may be labeled or unlabeled, depending on the specific variation employed, as described above. When the polynucleotide can form a stem-loop structure, it can be unlabeled when used to bind to a labeled target polynucleotide or amplification product therefrom, or the polynucleotide can be in the form of a molecular beacon and be used to bind to a target polynucleotide or amplification product therefrom which does not require a label.

The polynucleotide can bind to the target polynucleotide or amplification product produced therefrom, and a sample may be assayed for the presence of such a target polynucleotide or amplification product produced therefrom using the components of the kit.

A reagent for incorporating a label into an amplification product may be included in the kit, such as a labeled primer or nucleotide. The components of the kit are retained by a housing. Instructions for using the kit to perform a method of the invention are provided with the housing, and may be located inside the housing or outside the housing, and may be printed on the interior or exterior of any surface forming the housing which renders the instructions legible. An invader polynucleotide and/or a flap endonuclease can optionally be included in the kit for performing a cleavase assay. The kit may be in multiplex form, containing pluralities of one or more different substrates or encoded bead conjugates, and/or invader polynucleotides. The substrate may comprise a plurality of polynucleotides of different sequence for performing a plurality of individual assays thereon such as a microarray, or a plurality of different beads can be provided for a multiplexed assay wherein each of the different beads comprises a different polynucleotide for binding to a corresponding different target polynucleotide and/or amplification product.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

It is to be understood that while the invention has been described in conjunction with the preferred specific embodiments thereof, the foregoing description as well as the examples which follow are intended to illustrate and not limit the scope of the invention. Other aspects, advantages and modifications within the scope of the invention will be apparent to those skilled in the art to which the invention pertains.

Example 1

Spectrally Encoding and Functionalizing Microspheres

The following experiment was performed to prepare encoded and functionalized microspheres via a heat-swelling method and Dextran Biotin coating.

Materials:
a. 10 um Bangs COOH functionalized beads 10% solid (Bangs Lab)
b. 10 mM PBS, pH 7.4 (Sigma)
c. 10 mM PBS/1% BSA
d. Dihydrolipoic acid (DHLA)-derivatized SCNCs (Bawendi et al., PCT Publ. No. WO 00/17655)
e. Dextran Biotin 10 mg/mL (Sigma); Cat# B5512, Lot# 81H0080
f. Streptavidin 10 mg/mL (Pierce); Cat# 21 125B, Lot# AH41661

Protocol:
i. Wash beads three times with PBS buffer and resuspend in PBS to make 5% beads solution
ii. Heat bead solution in heat block up to 60–60° C. with constant mixing
iii. Add DHLA SCNCs (amount added depends on the intended intensity for the particular beads, determined empirically)
iv. Incubate the mixture of beads and SCNC for 5–10 min. at 60° C.
v. Wash encoded beads 3 times with PBS, resuspend in PBS. Check the intensity and uniformity of encoded beads with Facscan and Microscope
vi. Add Dextran Biotin (10 mg/mL) to encoded beads solution and incubate at room temperature overnight with constant mixing
vii. Wash biotin dextran-coated encoded beads with PBS and resuspend in PBS/BSA
viii. Add Streptavidin (final conc. of 5 mg/ml) to biotin-dextran-coated encoded beads and incubate at room temperature for 3–4 hours.
ix. Wash SA-encoded beads with PBS and resuspend in PBS/BSA.

SA-encoded beads are ready for attachment of biotinylated Molecular Beacon of choice.

2. Encoding Beads with DHLA SCNCs with BSA Absorption and Functionalizing beads with Streptavidin by Maleimide Conjugation

*BSA absorbed on beads provides surface for subsequent absorption of DHLA SCNCs and functional group for conjugation of Streptavidin.

Materials:
a. 10 um Bangs COOH beads 10% solid (Bangs Lab)
b. 10 mM PBS/1% BSA, pH 7.4
c. DHLA SCNCs (of different colors)
d. Sulfo-SMCC; Cat# 22322, Lot# AF40301, or Sulfo-SMPB (Pierce)
e. Conjugation buffer & Elution buffer for NAP5 column: 0.1M Sodium Phosphate, 0.15M NaCl, 10 mM EDTA, pH 7.2
f. NAP5 column equilibration buffer: 10 nM Sodium Phosphate, pH 6.8
g. NAP5 (Sephadex G25 resin, Pharmacia); Cat# 17–0853–02, Lot# 278694
h. Streptavidin (Pierce); Cat# 21125B, Lot# AH41661
i. 2-Iminothiolane (Sigma); Cat# I-6256, Lot# 128H1085

Protocol:
1. Wash beads 3 times with PBS
2. Add 1% BSA/PBS solution and incubate at room temperature overnight with constant mixing
3. Wash BSA-coated beads 3 times with PBS
4. Add DHLA SCNCs and incubate for 15–30 min @RT with constant mixing
5. Wash off excess DHLA SCNCs with PBS and resuspend [BSA encoded beads] in Conjugation buffer
   *Note: [BSA encoded beads] can be coated with another layer of BSA by incubating these beads with 1% BSA for several hours.
6. i. Add 2-iminothiolane (20 mg/mL) to [BSA encoded beads]solution. React @ RT for 1–2 hrs with constant mixing. Wash 3 times and resuspend with conjugation buffer
   ii. Maleimide activation of Steptavidin: to 20 mg/mL solution of Streptavidin (in conjugation buffer) added Sulfo-SMCC or Sulfo-SMPB (6 mg/mL). *Note: dissolve Sulfo-SMCC in samll amount of dH2O before adding to Streptavidin solution. React @RT for 30 min. (Timing this reaction with iminothiolane reaction above to get purified products at the same time.) Purify Maleimide-activated Streptavidin using NAP5 column with 10–15 mL equilibration buffer (pre-loading) and with 1–2 mL elution buffer (post-loading)

Mix purified products from two reactions above and react at Rt for 2–3 hrs. Wash SA-encoded beads with PBS and resuspend in PBS/BSA.

Example 2

Multiplex Molecular Beacon on a Bead Assay

To demonstrate that DNA assays can be multiplexed on encoded beads, four molecular beacons were chosen each attaches to different spectrally encoded encoded beads.

Preparation of Molecular Beacons:

Four molecular beacons of 25–27 bases in length having a 5 or 6 base pair stem were prepared; each was designed to recognize a different target. A biotin molecule was placed in the middle of each stem region for immobilization onto streptavidin-coated spectrally encoded beads. A fluorescein fluorophore was attached to the 5' end and [4-(4-dimethy-laminopherylazo) benzoic acid] (DABCYL) was attached at the 3' end of each molecular beacon. The polynucleotides forming the molecular beacons and their compliments were prepared by Midland Certified Reagent Company and are shown below, with the letter "c" designating the complement to the oligonucleotide name immediately following that designation.

Molecular Beacon on a Bead Assay

Two tubes were prepared each containing 50 uL of MB assay buffer with $10^4$ of each of the four different encoded microspheres conjugated to their respective molecular beacons. 2 uM of the complementary oligo for each of the four molecular beacons were added to one tube to open the molecular beacons by hybridization. The tubes were mixed continuously for 30 minutes in a 35° C. incubator and washed once with molecular beacon buffer. Approximately twenty to thirty thousand beads from each tube were transferred into a well in a 384 well plate and allowed to settled for at least 10 minutes. The encoded beads in each well were decoded and the signal intensity on each bead was measured. Twelve to 96 beads of each type were analyzed. FIG. 11 shows the average signal intensity for each population of encoded beads when the molecular beacons were closed or in the hairpin form and opened in the presence of complementary oligo as measured on a plate reader. Alternatively, these encoded beads can also be analyzed in a flow cytometer.

```
mbD7S8A (on 572 nm encoded beads): (SEQ ID NO: 1)
5'-(FLSN)GCAGC CCT TTC CCG GAA TGC GC(biotindT)GC (DABCYL)-3' cmb D7S8A: (SEQ ID NO: 2)
5'-TAT GAC CAG CAT TCC GGG AAA GGG AAG AAA-3' mbWNT5A (on 590 nm encoded beads): (SEQ ID NO: 3)
5'-(FLSN)GCACG CAC AAA CTG GTC CAC GA CG(biotindT)GC (DABCYL)-3' cmbWNT5A: (SEQ ID NO: 4)
5'-ACG GAG ATC GTG GAC CAG TTT GTG TGC AAG-3' mbG (on 630 nm encoded beads): (SEQ ID NO: 5)
5'-(FLSN)GCGAGC CAC CAA AGA TGA TAT GC(biotindT)CGC (DABCYL)-3' cmbG: (SEQ ID NO: 6)
5'-AAA GAA AAT ATC ATC TTT GGT GTT TCC TAT-3' mbT (on 572 + 616 nm encoded beads): (SEQ ID NO: 7)
5'-(FLSN)GCGAGC CAC CAA ATA TGA TAT GC(biotindT)CGC (DABCYL)-3' cmbG: (SEQ ID NO: 8)
5'-AAA GAA AAT ATC ATA TTT GGT GTT TCC TAT-3'
```

Attaching Molecular Beacons on Streptavidin-Coated Encoded Beads mbD7S8A was attached to beads encoded with 572 nm emitting SCNCs, mbWNT5A was attached to beads encoded with 590 nm emitting SCNCs, mbG was attached to beads encoded with 620 nm emitting SCNCs, and mbT was attached to a mixture beads encoded with 572 nm and 616 nm emitting SCNCs as shown in Table 1. Approximately $5 \times 10^5$ streptavidin-coated beads were continuously mixed in 75 uL of 1×PBS, 1% BSA, 2 uM of molecular beacon for 2 hours. The SCNCs were washed with PBS to remove the excess unconjugated molecular beacons and then resuspended in MB assay buffer (20 mM Tris HCl, 50 mM KCl, 5 mM MgCl2, pH 8.0).

Results demonstrate a simple four-plex assay for detecting unlabeled DNA on encoded beads conjugated to molecular beacons. The hybridization is fast and the assay can be use to monitored a much larger number of DNA probes by increasing the number of encoded bead conjugates easily.

Example 3

Loop Probe Hybridization on Encoded Beads

The reason for using loop probes hybridized to beads was to increase the specificity of allele specific hybridization for SNP detection. To do this we took advantage of the secondary structure of the loop probe oligonucleotide to increase the specificity to get single base discrimination in the hybridization assay.

```
Loop Probe Oligonucleotides Used:
LDLr        Loop A-5' amino-CGAGCATATGGTCCTCTTCCGCTCG
            (SEQ ID NO: 9)
```

```
                    -continued
LDLr       Loop B-5-5' amino-CGAGCATATGGTTCTCTTCCGCTCG
           (SEQ ID NO: 10)

Complementary Target Oligonucleotides:
LDLr test A  5' fl-CCCAGTGTGGAAGAGGACCATATCCTCTGGG
             (SEQ ID NO: 11)

LDLr test B  5' fl-CCCAGTGTGGAAGAGAACCATATCCTCTGGG
             (SEQ ID NO: 12)

PCR Primers:
LDLrsb     5' biotin tcacaggttccgatgtcaac
           (SEQ ID NO: 13)

LDLrab     5' biotin cagggtggtcctctcacac
           (SEQ ID NO: 14)
```

Figure 12:
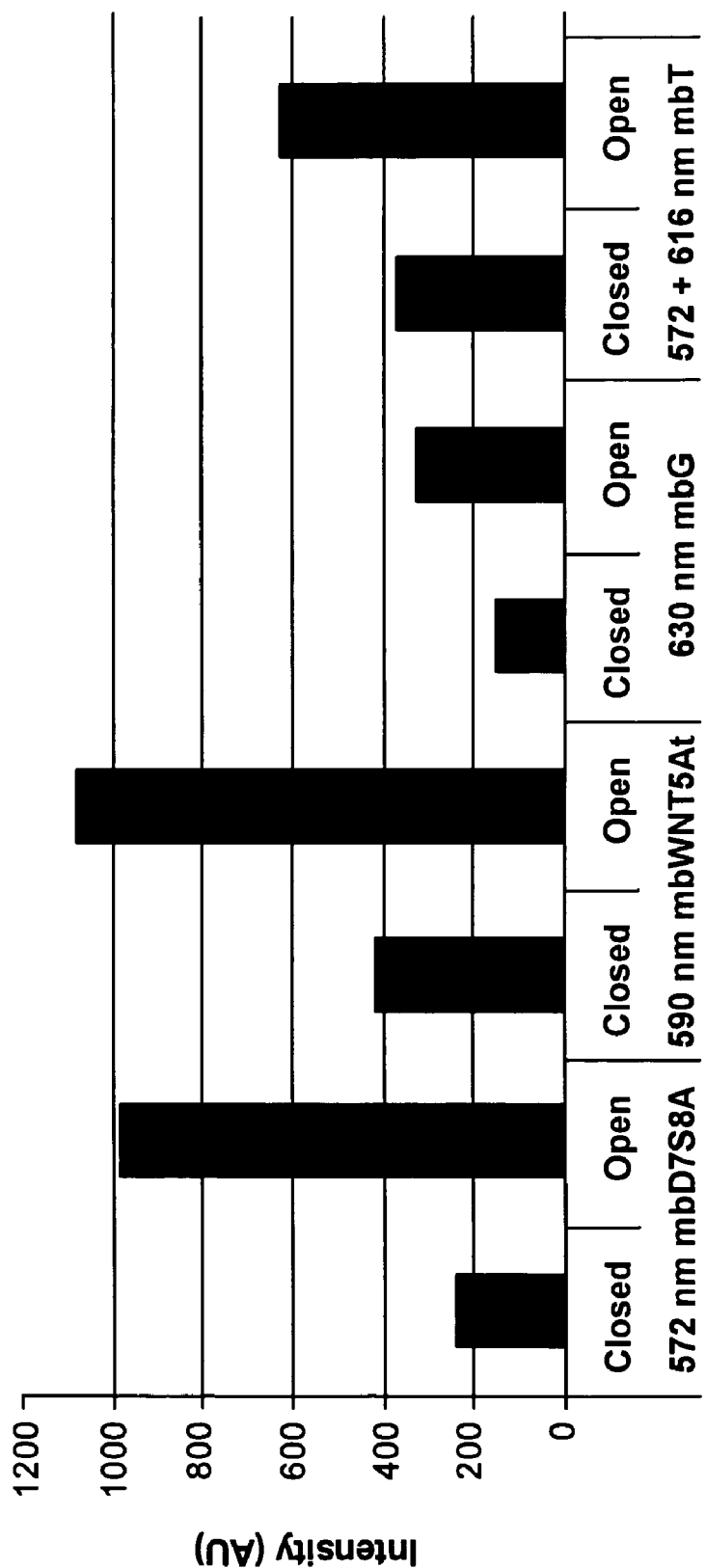
FIG. 12. Four molecular beacons on different types of encoded beads without their complementary sequences (MB closed and quenched)-added and with their complementary sequences (MB opened and unquenched) were assayed. The encoded bead conjugates in each tube were analyzed using a plate reader. Twelve to 96 of each type of conjugate from each tube was read. Each bar shows the intensity of the beads in arbitrary units, with the top section showing the standard deviation.

The specificity of single base mismatch detection by loop oligo hybridization was tested by hybridization of fluorescein labeled complementary target oligos to encoded beads conjugated to loop probe oligos. The loop probes and the complementary oligo sequences are shown above. The beads were conjugated with oligos by conventional EDC conjugation methods by incubating 2 ul of a 100 uM solution of 5'amino-modified oligos with approximately 1 million either 6 u or 10 u carboxylate-modified beads in 200 mM EDC for 4 hours at room temperature. Then the unconjugated oligo was washed away with 2×SSC, 0.5% SDS. The hybridization was done by adding 2.5 ul of 5' fluorescein modified complementary oligo and 1 ul of 10 u conjugated beads (~50,000) to 40 ul hybridization buffer: 5 mM MgCl$_2$, 20 mM Tris pH 8.0, 50 mM KCl. The beads were incubated with oligo for 2 hours at 45° C. Then the beads with complementary oligo were spun down and resuspended in 400 ul PBS pH 7.4. The samples were read on a flow cytometer in PBS. The results can be seen in FIG. 12. The one base mismatch was enough to distinguish the A allele from the B allele in the hybridization of the complementary fluorescein modified oligo conjugated bead assay.

Figure 13:
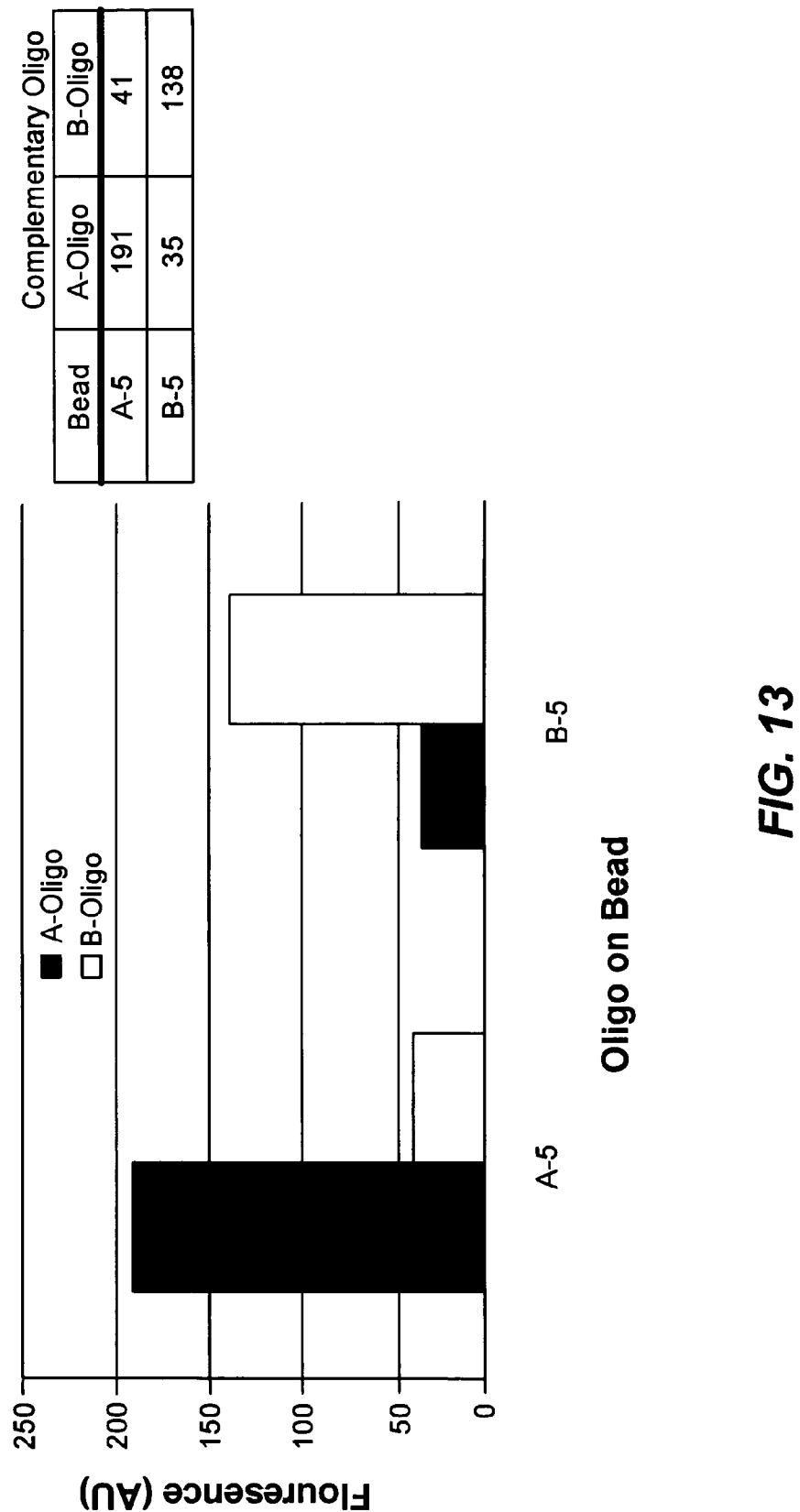
FIG. 13 shows the hybridization of the correct target oligonucleotides exhibiting a single nucleotide polymorphism to the corresponding loop probes conjugated to spectrally encoded 10 micron microspheres. Allele-specific preferential hybridization was observed.

The region of the genome containing the SNP of interest was amplified by PCR. The sequence of the PCR primers is shown above. The PCR product was hybridized to the same loop oligo-conjugated beads described above. The hybridization was preformed by adding 2.5 μl of amplicon to 40 μl hybridization buffer: 5 mM MgCl$_2$, 20 mM Tris pH 8.0, 50 mM KCl and heat denatured it at 95° C. for 3 minutes. The amplicon was snap cooled by putting on ice for 5 minutes before adding to 1 μl of 10μ conjugated beads (~50,000). The beads were incubated with amplicon for 2 hours at 45° C. Then the beads with amplicon were spun down and resuspended in 100 μl PBS/BSA. To the PBS/BSA 1 μl of a 0.1 mg/ml SA-PE was added and incubated at room temperature for 30 minutes. All the beads were spun down, the supernatant removed and the samples were resuspended in PBS pH 7.4. Samples were read on a flow cytometer in 400 μl PBS. FIG. 13 shows that the proper allele discrimination is seen for both the wildtype and the mutant genotype samples.

Example 4

Detection of D7S8 SNP Using Molecular Beacons on a Bead

This experiment was performed to demonstrate the detection of a SNP at the human genomic D7S8 locus at chromosomal location: 7q22–31.1, a cystic fibrosis related gene Sequence (151 bp) spanning the D7S8 locus:

```
Upper strand: (SEQ ID NO: 15)
5'-CTA GGG ATG TTC CTG TCT CAG GGA CCC TGA CCT TAT TGC TCC CCT TTC

CXG GAA TGC TGG TCC TGA CAC AAT AAT ATA AGC TCT GAG AAG GCA GCC ATT

TTT GTA TGC TTT ACT CCA GGG TAC TTC TCA ACT CGC AGA ACA GGG CTT GGC

A-3'

Lower strand: (SEQ ID NO: 16)
3'-GAT CCC TAG AAG GAG AGA GTG CCT GGG ACT GGA ATA ACG AGG GGA

AAG GXC CTT ACG ACC AGG ACT GTG TTA TTA TAT TCG AGA CTC TTC CGT CGG

TAA AAA CAT ACG AAA TGA GGT CCG ATG AAG AGT TGA GCG TCT TGT CCC

GAA CCG T-3 5'
```

X: location of SNP
X=C/G: Allele A
X=T/A: Allele B

Materials:
1. Genomic DNAs: GM09947A, GM09948A, SS
2. 4% Agarose (_EtBr) Gel (Invitrogen); Cat# 45–0009, Lot# F24020
3. 10 kD Centricon (Pall Filtron); Cat# OD010C33, Lt# 9252D 4. Streptavidin encoded beads (prepared using BSA/ DHLASCNC/Maleimide conjugation method)
5. 76bp fragment PCR primers:

```
Forward primer:    5'-biotin-G GGA CCC TGA CCT TAT TGC-3'
                   (SEQ ID NO: 17)

Reverse primer:    3'-TCG AGA CTC TTC CGT CGG T-biotin-5'
                   (SEQ ID NO: 18)
```

6. 151 bp fragment PCR primers:

```
Forward primer:    5'-biotin-CTA GGG ATG TTC CTG TCT CAG-3'
                   (SEQ ID NO: 19)

Reverse primer:    3'-'A GCG TCT TGT CCC GAA CCG T-biotin-5'
                   (SEQ ID NO: 20)
```

7. mbD7S8A (Midland Certified): (SEQ ID NO: 1)
5'-Fl-GCAGCCCT\TTC CCG GAA TGC GC(biotindT)GC-dabcyl-3' mbD7S8B (SEQ ID NO: 21)
5'-Fl-GCAGC(CT\TTC CTG GAA TGC GC(biotindT)GC-dabcyl-3'

Complementary D7S8A: (SEQ ID NO: 2)
5'-TAT GAC CAG CAT TCC GGG AAA GGG AAG AAA-3'

Complementary D7S8B: (SEQ ID NO: 22)
5'-TAT GAC CAG CAT TCC AGG AAA GGG AAG AAA-3'

8. Linear probes for covalent conjugation of oligos on beads:

```
AminoD7S8A:    5'NH2-TTT TTT ACC AGC ATT CCG GGA AAG-3'
               (SEQ ID NO: 25)

AminoD7S8B:    5'NH2-TTT TTT ACC AGC ATT CCA GGA AAG-3'
               (SEQ ID NO: 26)
```

9. PCR reaction mix:

a. AmpliTaq DNA polymerase 5 U/uL
  b. dNTP mix 10 mM
  c. 10×PCR buffer II
  d. MgCl2 solution 25 mM All components are from Perkin-Elmer
  Preparation of PCR Reaction Mix:
  399 uL of autoclaved water
  15 uL of 5U/uL of AmpliTaq
  60 uL of 10×PCR buffer II
  96 uL of 25 mM MgCl2
  30 uL of 10 mM dNTP mix
  Total volume: 600 uL PCR Conditions:

A. Symmetrical PCR Reaction Volume and Content:
  10 uL of DNA (0.5 ng/uL)
  20 uL of PCR reaction mix
  10 uL of Forward primer (2.5 uM)
  10 uL of Reverse primer (2.5 uM)
  Denaturation: 95° C. for 1 min.
  36 cycles of (95° C. for 30 sec., 63° C. (for 151 bp PCR) or 58° C. (for 76 bp PCR) 72° C. for 30 sec.)
  Termination: 72° C. for 10 min. then cool down to 4° C.
  Double-stranded product of 151 bp and 76 bp are confirmed by 4% gel with 20 bp ladder standard.

B. Asymmetrical PCR Reaction Volume and Content:
  10 uL of 1/10 dilution of purified 76 bp fragment (110 kD) Centricon's retentate)
  20 uL of PCR reaction mix
  20 uL of Reverse Primer (2.5 uM)
  Denaturation: 95° C. for 1 min.
  40 cycles of (95° C. for 30 sec., 50° C. for 30 sec, 72° C. for 30 sec.)
  Termination: 72° C. for 10 min. then cool down to 4° C.

Single-strand PCR product was verified by both 4% Agarose Gel and linear probe assay of covalently conjugated beads of Amino D7S8A and Amino D7S8B with asymmetric PCR product using 76 bp fragment PCR forward primers.

mbD7S8A was attached to Orange encoded beads through a streptavidin-biotin link.

mbD7S8B was attached to Red encoded beads through a streptavidin-biotin link.

The mbD7S8A-Orange encoded beads were titrated with different concentrations of D7S8A and D7S8B to determine the dynamic range of the assay. 0.1 uM of greater of the amplicon (dynamic range of the assay) was needed to generate enough signals significantly above from the background.

Allelic Discrimination of Three Genomic DNAs at D7S8 Locus:

Assay Condition:
  Three 50 uL mixtures of mbD7S8A Orange encoded beads and mbD7S8B Red encoded beads are incubated at 35° C. for 5 min. (total of about 20,000 beads per tube)

Add concentrated (5 tubes of asymmetrical PCR product) 76b amplicons of 09947A or 09948A or SS to each tube separately. Incubate for 15 min. at 35° C.

To each tube add 300 uL of MB assay buffer. Read 2000 beads from each tube separately on FACSCAN. Plot FL1 signal from Red and Orange beads for three DNA samples.

Figure 14:
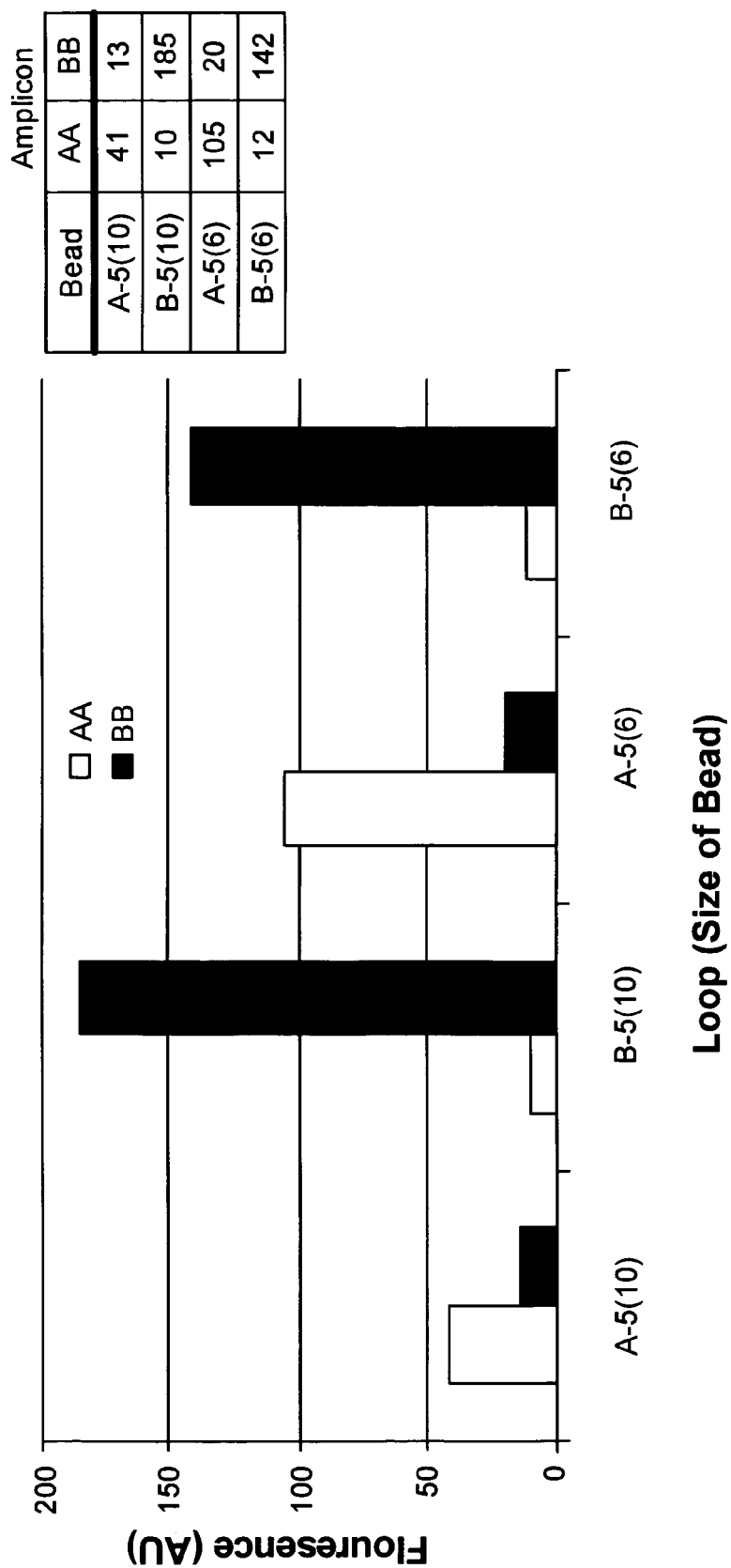
FIG. 14 shows graphical results of the hybridization of PCR products from the genomic locus exhibiting the SNP shown in FIG. 12 on either 10 u or 6 u beads. Allele-specific detection of the target genotype was observed.
Figure 15:
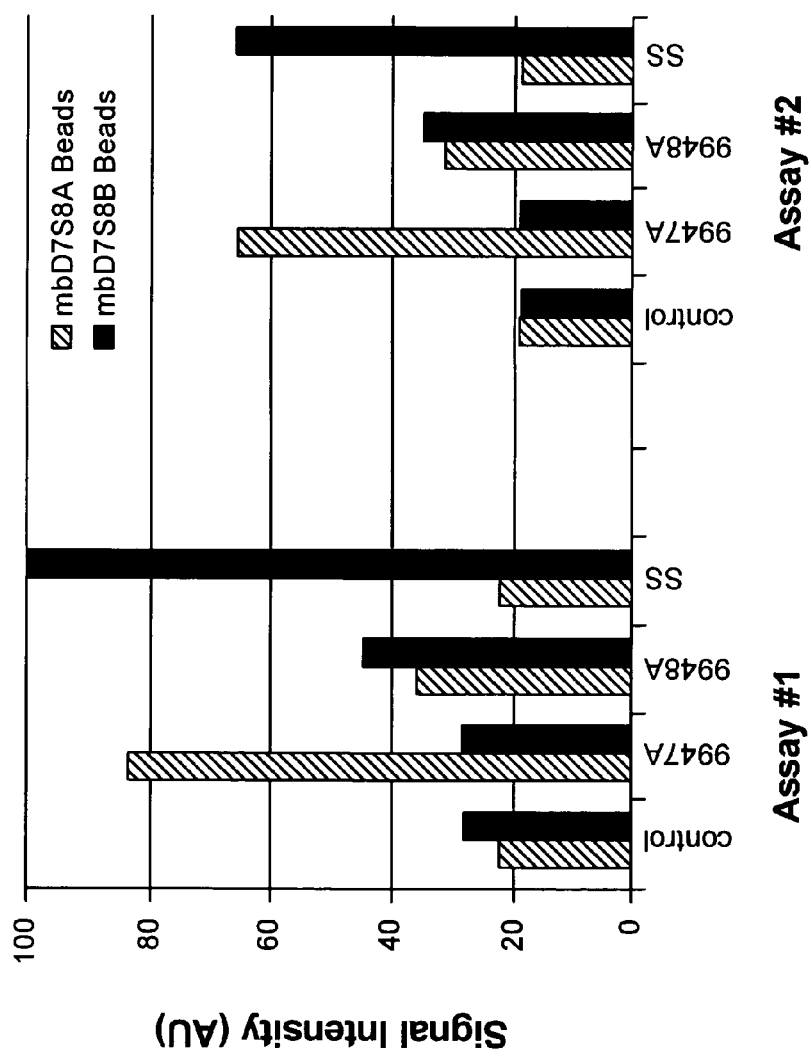
FIG. 15 shows graphical results of a molecular beacon on a bead assay demonstrating discriminating detection of two alleles of a SNP from a genomic locus using allele-specific molecular beacons.

The results are shown in FIG. 14.

Conclusion:

A molecular beacon on encoded beads assay was able to detect the SNP at the D7S8 locus with allelic specificity, and provide an alternative assay for SNP detection that permits multiplex assays to be performed due to the wide range of SCNC codes available. A Molecular Beacon on encoded beads assay allows real-time, low temperature, and one-step assay with a short assay time. Another special feature of this assay format is that there is no need to incorporate a label during a PCR.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

---

What is claimed is:

1. A kit comprising:
a substrate attached to an unlabeled probe polynucleotide comprising first and second complementary regions and a third region located between the first and second complementary regions, wherein the probe polynucleotide can form a stem-loop structure in which the first and second complementary regions hybridize to each other to form a stem and the third region forms a loop, wherein at least a part of the third region is complementary to at least a part of a capture sequence of an amplification product from a target polynucleotide, wherein the unlabeled probe polynucleotide can preferentially hybridize to the amplification product and thereby disrupt formation of the stem-loop structure under at least one set of hybridization conditions;
a reagent for incorporating a label into the amplification product;
a housing for retaining the substrate and the reagent; and
instructions provided with said housing that describe how to use the components of the kit to assay a sample for the amplification product.

2. The kit of claim 1, wherein the reagent is a labeled nucleotide.

3. The kit of claim 1, wherein the reagent is a labeled primer.

4. The kit of claim 1 wherein the substrate is attached to a plurality of different unlabelled probe polynucleotides, wherein each of said different unlabelled probe polynucleotides is attached at an identifiable location on the substrate, wherein each of said different probe polynucleotides can preferentially hybridize to a corresponding different amplification product, each of said corresponding different amplification products comprising a label that can be the same or different as the label on the other corresponding different amplification products, wherein each of said different probe polynucleotides comprises first and second complementary regions and a third region located between the first and second complementary regions, and further wherein each of said different probe polynucleotides can form a stem-loop structure in which, the first and second complementary regions hybridize to each other to form a stem and the third region forms a loop, wherein at least a part of the third region of each of said different probe polynucleotides is complementary to at least a part of its corresponding different amplification product, and wherein each of said different probe polynucleotides can preferentially hybridize to its corresponding different amplification product and thereby disrupt formation of its stem-loop structure under at least one set of hybridization conditions, and wherein said instructions further describe how to use the components of the kit to assay the sample for each of said corresponding different amplification products.

* * * * *

SEQUENCE LISTING

```
<160> NUMBER OF SEQ ID NOS: 24

<210> SEQ ID NO 1
<211> LENGTH: 25
<212> TYPE: DNA
<213> ORGANISM: Artificial
<220> FEATURE:
<223> OTHER INFORMATION: mbD7S8A
<220> FEATURE:
<221> NAME/KEY: misc_feature
<222> LOCATION: (23)..(23)
<223> OTHER INFORMATION: N = (biotin dT)

<400> SEQUENCE: 1
gcagcccttt cccggaatgc gcngc                                    25

<210> SEQ ID NO 2
<211> LENGTH: 30
<212> TYPE: DNA
<213> ORGANISM: Artificial
<220> FEATURE:
<223> OTHER INFORMATION: cmb D7S8A

<400> SEQUENCE: 2
tatgaccagc attccgggaa agggaagaaa                               30

<210> SEQ ID NO 3
<211> LENGTH: 27
<212> TYPE: DNA
<213> ORGANISM: Artificial
<220> FEATURE:
<223> OTHER INFORMATION: mbWNT5A
<220> FEATURE:
<221> NAME/KEY: misc_feature
<222> LOCATION: (25)..(25)
<223> OTHER INFORMATION: N = (biotin dT)

<400> SEQUENCE: 3
gcacgcacaa actggtccac gacgngc                                  27

<210> SEQ ID NO 4
<211> LENGTH: 30
<212> TYPE: DNA
<213> ORGANISM: Artificial
<220> FEATURE:
<223> OTHER INFORMATION: cmbWNT5A

<400> SEQUENCE: 4
acggagatcg tggaccagtt tgtgtgcaag                               30

<210> SEQ ID NO 5
```

```
<211> LENGTH: 27
<212> TYPE: DNA
<213> ORGANISM: Artificial
<220> FEATURE:
<223> OTHER INFORMATION: mbG
<220> FEATURE:
<221> NAME/KEY: misc_feature
<222> LOCATION: (24)..(24)
<223> OTHER INFORMATION: N = (biotin dT)

<400> SEQUENCE: 5
gcgagccacc aaagatgata tgcncgc                                     27

<210> SEQ ID NO 6
<211> LENGTH: 30
<212> TYPE: DNA
<213> ORGANISM: Artificial
<220> FEATURE:
<223> OTHER INFORMATION: cmbG

<400> SEQUENCE: 6
aaagaaaata tcatctttgg tgtttcctat                                  30

<210> SEQ ID NO 7
<211> LENGTH: 27
<212> TYPE: DNA
<213> ORGANISM: Artificial
<220> FEATURE:
<223> OTHER INFORMATION: mbT
<220> FEATURE:
<221> NAME/KEY: misc_feature
<222> LOCATION: (24)..(24)
<223> OTHER INFORMATION: N = (biotin dT)

<400> SEQUENCE: 7
gcgagccacc aaatatgata tgcncgc                                     27

<210> SEQ ID NO 8
<211> LENGTH: 30
<212> TYPE: DNA
<213> ORGANISM: Artificial
<220> FEATURE:
<223> OTHER INFORMATION: cmbT

<400> SEQUENCE: 8
aaagaaaata tcatatttgg tgtttcctat                                  30

<210> SEQ ID NO 9
<211> LENGTH: 25
<212> TYPE: DNA
<213> ORGANISM: Artificial
<220> FEATURE:
<223> OTHER INFORMATION: LDLr Loop A-5

<400> SEQUENCE: 9
cgagcatatg gtcctcttcc gctcg                                       25

<210> SEQ ID NO 10
<211> LENGTH: 25
<212> TYPE: DNA
<213> ORGANISM: Artificial
<220> FEATURE:
<223> OTHER INFORMATION: LDLr Loop B-5

<400> SEQUENCE: 10
cgagcatatg gttctcttcc gctcg                                       25
```

```
<210> SEQ ID NO 11
<211> LENGTH: 31
<212> TYPE: DNA
<213> ORGANISM: Artificial
<220> FEATURE:
<223> OTHER INFORMATION: LDLr test A

<400> SEQUENCE: 11
cccagtgtgg aagaggacca tatcctctgg g                              31

<210> SEQ ID NO 12
<211> LENGTH: 31
<212> TYPE: DNA
<213> ORGANISM: Artificial
<220> FEATURE:
<223> OTHER INFORMATION: LDLr test B

<400> SEQUENCE: 12
cccagtgtgg aagagaacca tatcctctgg g                              31

<210> SEQ ID NO 13
<211> LENGTH: 20
<212> TYPE: DNA
<213> ORGANISM: Artificial
<220> FEATURE:
<223> OTHER INFORMATION: LDLrsb

<400> SEQUENCE: 13
tcacaggttc cgatgtcaac                                           20

<210> SEQ ID NO 14
<211> LENGTH: 19
<212> TYPE: DNA
<213> ORGANISM: Artificial
<220> FEATURE:
<223> OTHER INFORMATION: LDLrab

<400> SEQUENCE: 14
cagggtggtc ctctcacac                                            19

<210> SEQ ID NO 15
<211> LENGTH: 151
<212> TYPE: DNA
<213> ORGANISM: Artificial
<220> FEATURE:
<223> OTHER INFORMATION: Sequence spanning the D7S8 locus upper strand
<220> FEATURE:
<221> NAME/KEY: misc_feature
<222> LOCATION: (50)..(50)
<223> OTHER INFORMATION: N: Location of SNPN=C/G: Allele AN=T/A:
      Allele B

<400> SEQUENCE: 15
ctagggatgt tcctgtctca gggaccctga ccttattgct cccctttccn ggaatgctgg    60
tcctgacaca ataataaag ctctgagaag gcagccattt ttgtatgctt tactccaggc   120
tacttctcaa ctcgcagaac agggcttggc a                                 151

<210> SEQ ID NO 16
<211> LENGTH: 151
<212> TYPE: DNA
<213> ORGANISM: Artificial
<220> FEATURE:
<223> OTHER INFORMATION: Sequence spanning the D7S8 locus lower strand
<220> FEATURE:
<221> NAME/KEY: misc_feature
<222> LOCATION: (102)..(102)
<223> OTHER INFORMATION: N: location of SNPN=C/G: Allele AN=T/A:
```

-continued

Allele B

<400> SEQUENCE: 16
tgccaagccc tgttctgcga gttgagaagt agcctggagt aaagcataca aaaatggctg    60
ccttctcaga gcttatatta ttgtgtcagg accagcattc cnggaaaggg gagcaataag   120
gtcagggtcc ctgagacagg aacatcccta g                                  151

<210> SEQ ID NO 17
<211> LENGTH: 19
<212> TYPE: DNA
<213> ORGANISM: Artificial
<220> FEATURE:
<223> OTHER INFORMATION: 76bp fragment PCR forward primer

<400> SEQUENCE: 17
gggaccctga ccttattgc                                                 19

<210> SEQ ID NO 18
<211> LENGTH: 19
<212> TYPE: DNA
<213> ORGANISM: Artificial
<220> FEATURE:
<223> OTHER INFORMATION: 76bp fragment PCR reverse primer

<400> SEQUENCE: 18
tggctgcctt ctcagagct                                                 19

<210> SEQ ID NO 19
<211> LENGTH: 21
<212> TYPE: DNA
<213> ORGANISM: Artificial
<220> FEATURE:
<223> OTHER INFORMATION: 151bp fragment PCR forward primer

<400> SEQUENCE: 19
ctagggatgt tcctgtctca g                                              21

<210> SEQ ID NO 20
<211> LENGTH: 20
<212> TYPE: DNA
<213> ORGANISM: Artificial
<220> FEATURE:
<223> OTHER INFORMATION: 151bp fragment PCR reverse primer

<400> SEQUENCE: 20
tgccaagccc tgttctgcga                                                20

<210> SEQ ID NO 21
<211> LENGTH: 25
<212> TYPE: DNA
<213> ORGANISM: Artificial
<220> FEATURE:
<223> OTHER INFORMATION: mbD7S8B
<220> FEATURE:
<221> NAME/KEY: misc_feature
<222> LOCATION: (23)..(23)
<223> OTHER INFORMATION: N = (biotin dT)

<400> SEQUENCE: 21
gcagcccttt cctggaatgc gcngc                                          25

<210> SEQ ID NO 22
<211> LENGTH: 30
<212> TYPE: DNA
<213> ORGANISM: Artificial

-continued

```
<220> FEATURE:
<223> OTHER INFORMATION: Complementary D7S8B

<400> SEQUENCE: 22
tatgaccagc attccaggaa agggaagaaa                                    30

<210> SEQ ID NO 23
<211> LENGTH: 24
<212> TYPE: DNA
<213> ORGANISM: Artificial
<220> FEATURE:
<223> OTHER INFORMATION: AminoD7S8A

<400> SEQUENCE: 23 tttttttacca gcattccggg aaag                                         24

<210> SEQ ID NO 24
<211> LENGTH: 24
<212> TYPE: DNA
<213> ORGANISM: Artificial
<220> FEATURE:
<223> OTHER INFORMATION: AminoD7S8B

<400> SEQUENCE: 24 tttttttacca gcattccagg aaag                                         24
```